(12) United States Patent
Stubenrauch

(10) Patent No.: US 11,561,229 B2
(45) Date of Patent: Jan. 24, 2023

(54) IMMUNOASSAY FOR THE DETERMINATION OF FC-REGION MODIFIED ANTIBODIES

(71) Applicant: Hoffmann-La Roche Inc., Little Falls, NJ (US)

(72) Inventor: Kay-Gunnar Stubenrauch, Penzberg (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 543 days.

(21) Appl. No.: 15/988,939

(22) Filed: May 24, 2018

(65) Prior Publication Data

US 2018/0364251 A1    Dec. 20, 2018

Related U.S. Application Data

(63) Continuation of application No. PCT/EP2016/079086, filed on Nov. 29, 2016.

(30) Foreign Application Priority Data

Nov. 30, 2015    (EP) .................................... 15197058

(51) Int. Cl.
| | | |
|---|---|---|
| *G01N 33/53* | (2006.01) | |
| *G01N 33/68* | (2006.01) | |
| *G01N 33/558* | (2006.01) | |
| *G01N 33/543* | (2006.01) | |

(52) U.S. Cl.
CPC ... *G01N 33/6854* (2013.01); *G01N 33/54353* (2013.01); *G01N 33/558* (2013.01)

(58) Field of Classification Search
CPC .......... G01N 33/558; G01N 33/54353; G01N 33/581; G01N 33/6854; G01N 2470/00; G01N 2470/04; G01N 2470/06; G01N 2470/10; G01N 2470/12
See application file for complete search history.

(56) References Cited

U.S. PATENT DOCUMENTS

2004/0242848 A1 * 12/2004 Owens .................... C07K 16/44
                                                                        530/387.3

FOREIGN PATENT DOCUMENTS

| EP | 0 307 434 B1 | 9/1993 | |
|---|---|---|---|
| EP | 0 307 434 B2 | 9/1993 | |
| EP | 1845378 A1 | 10/2007 | |
| JP | H01-223351 A | 9/1989 | |
| JP | H01223351 A | 9/1989 | |
| RU | 2296332 * | 3/2007 | ............. G01N 33/53 |
| WO | 96/22533 A1 | 7/1996 | |
| WO | 2011117329 A1 | 9/2011 | |
| WO | 2014006124 A1 | 1/2014 | |
| WO | 2014009474 A1 | 1/2014 | |
| WO | 2015101587 A1 | 7/2015 | |

OTHER PUBLICATIONS

Thermo Scientific ELISA Guide (2008; retrieved from http://tools.thermofisher.com/content/sfs/brochures/1602127-Assay-Development-Handbook.pdf).*
CD Creative Diagnostics (2009; retrieved from https://www.creative-diagnostics.com/Phencyclidine-HRP-Conjugated-124059-219.htm).*
Digoxygenin Conjugates (CD Creative Diagnostics;2009;retrieved from https://www.creative-diagnostics.com/Digoxigenin-HRP-conjugated-105650-219.htm).*
Mire-Sluis et al. (Journal of Immunological Methods 289 (2004), pp. 1-16).*
Butler et al., "Solid Supports in Enzyme-Linked Immunosorbent Assay and Other Solid-Phase Immunoassays" Methods 22:4-23 ( 2000).
Database WPI Week 198942 Thomson Scientific, London, GB; AN 1989-303835 XP002758038, —& JP H01 223351 A (Dainippon Pharm Co Ltd) Sep. 6, 1989) abstract.
Hage et al., "Immunoassays" Anal. Chem. 71:294R-304R ( 1999).
Hermanson, et al. Bioconjugate Techniques "Antibody Modification and Conjugation" San Diego:Academic Press, Inc.,:456 ( 1996).
International Search Report for PCT/EP2016/079086 dated Feb. 6, 2017.
International Preliminary Report on Patentability (IPRP) for PCT/EP2016/079086 dated Jun. 5, 2018.
Lu et al., "Oriented Immobilization of Antibodies and Its Applications in Immunoassays and Immunosensors" Analyst 121:29R-32R ( 1996).
Lund et al., "Oligosaccharide-protein interactions in IgG can modulate recognition by Fcγ receptors" FASEB J 9:115-119 ( 1995).
Martin et al., "Peer Reviewed: Nanomaterials in Analytical Chemistry" Analytical Chemistry News & Features 70:322A-327A (May 1, 1998).
Morgan et al., "The N-terminal end of the $C_H2$ domain of chimeric human IgG1 anti-HLA-DR is necessary for C1q, FcγRI and RcγRIII binding" Immunol 86(2):319-324 ( 1995).
Shields et al. et al., "High resolution mapping of the binding site on human IgG1 for Fc gamma RI, Fc gamma RII, Fc gamma RIII, and FcRn and design of IgG1 variants with improved binding to the Fc gamma R" J Biol Chem 276(9):6591-6604 (Mar. 2, 2001).

(Continued)

*Primary Examiner* — Carmencita M Belei

(57) ABSTRACT

Herein is reported a method for the determination of the amount of a bivalent antibody in a serum or plasma sample obtained from a non-human experimental animal, whereby the antibody comprises one or more mutations in the Fc-region compared to the corresponding wild-type Fc-region that has a sequence of SEQ ID NO: 01, 02, or 03, wherein the method comprises the following steps a) immobilizing a non-antibody polypeptide to which more than one copy of the antigen of the antibody is covalently conjugated on a solid surface, b) incubating the immobilized antigen with the sample to form an immobilized antigen-antibody complex, c) incubating the immobilized antigen-antibody complex with the antigen conjugated to a detectable label to form an immobilized ternary complex, and d) determining the amount of the antibody by determining the amount of the detectable label in the immobilized ternary complex.

6 Claims, 5 Drawing Sheets

Specification includes a Sequence Listing.

(56) References Cited

OTHER PUBLICATIONS

The English translation of the Japanese Office Action, dated Sep. 30, 2020, in the related Japanese Appl. No. 2018-546758.
Chinese Office Action, dated Aug. 14, 2020, in the related Chinese Appl. No. 201680067452.9, including English translation.
The Chinese Office Action, dated Mar. 22, 2021, in the related Chinese Appl. No. 201680067452.9.
Medical Immunology edited by Liu Wentai, China Press of Traditional Chinese Medicine, Feb. 2009, pp. 220, 224.
Gong et al., Practical Experimental Technology of Fundamental Medicine, Press of Jilin Science and Technology, Apr. 1991, pp. 107-108.
The Chinese Office Action, dated Jun. 30, 2021, in the related Chinese Appl. No. 201680067452.9.
Qiuyan Tang, editor-in-chief, "Practical Technology of Immunodiagnostic Reagents," China Ocean Press, p. 106, published on Aug. 2009. (Partial English translation included.).
John R. Crowther, editor-in-chief, "The ELISA Guidebook, 2nd edition," Humanan Press, pp. 79-110, Chapter 4 "Titration of Reagents", published in 2009.

* cited by examiner

SEQUENCE LISTING

<160> NUMBER OF SEQ ID NOS: 8

<210> SEQ ID NO 1
<211> LENGTH: 330
<212> TYPE: PRT
<213> ORGANISM: Homo sapiens

<400> SEQUENCE: 1

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 2
<211> LENGTH: 330
<212> TYPE: PRT
<213> ORGANISM: Homo sapiens

<400> SEQUENCE: 2

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 3
<211> LENGTH: 327
<212> TYPE: PRT
<213> ORGANISM: Homo sapiens

<400> SEQUENCE: 3

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
             35                   40                  45

Gly Val His Thr Phe Pro Ala Val Leu Gln Ser Ser Gly Leu Tyr Ser
 50                   55                  60

Leu Ser Ser Val Val Thr Val Pro Ser Ser Ser Leu Gly Thr Lys Thr
 65                   70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Ser Cys Pro Ala Pro
             100                 105                 110

Glu Phe Leu Gly Gly Pro Ser Val Phe Leu Phe Pro Pro Lys Pro Lys
             115                 120                 125

Asp Thr Leu Met Ile Ser Arg Thr Pro Glu Val Thr Cys Val Val Val
             130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                 165                 170                 175

Asn Ser Thr Tyr Arg Val Val Ser Val Leu Thr Val Leu His Gln Asp
             180                 185                 190

Trp Leu Asn Gly Lys Glu Tyr Lys Cys Lys Val Ser Asn Lys Gly Leu
             195                 200                 205

Pro Ser Ser Ile Glu Lys Thr Ile Ser Lys Ala Lys Gly Gln Pro Arg
             210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                 245                 250                 255

Ile Ala Val Glu Trp Glu Ser Asn Gly Gln Pro Glu Asn Asn Tyr Lys
             260                 265                 270

Thr Thr Pro Pro Val Leu Asp Ser Asp Gly Ser Phe Phe Leu Tyr Ser
             275                 280                 285

Arg Leu Thr Val Asp Lys Ser Arg Trp Gln Glu Gly Asn Val Phe Ser
             290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 4
<211> LENGTH: 4
<212> TYPE: PRT
<213> ORGANISM: Artificial Sequence
<220> FEATURE:
<223> OTHER INFORMATION: GGGS linker unit

<400> SEQUENCE: 4

Gly Gly Gly Ser
1

<210> SEQ ID NO 5
<211> LENGTH: 5
<212> TYPE: PRT
<213> ORGANISM: Artificial Sequence
<220> FEATURE:
<223> OTHER INFORMATION: GGGGS linker unit

<400> SEQUENCE: 5

```
Gly Gly Gly Gly Ser
1               5

<210> SEQ ID NO 6
<211> LENGTH: 5
<212> TYPE: PRT
<213> ORGANISM: Artificial Sequence
<220> FEATURE:
<223> OTHER INFORMATION: QQQQG linker unit

<400> SEQUENCE: 6

Gln Gln Gln Gln Gly
1               5

<210> SEQ ID NO 7
<211> LENGTH: 5
<212> TYPE: PRT
<213> ORGANISM: Artificial Sequence
<220> FEATURE:
<223> OTHER INFORMATION: SSSSG linker unit

<400> SEQUENCE: 7

Ser Ser Ser Ser Gly
1               5

<210> SEQ ID NO 8
<211> LENGTH: 17
<212> TYPE: PRT
<213> ORGANISM: Artificial Sequence
<220> FEATURE:
<223> OTHER INFORMATION: GSSSSSSSSSSSSSSSG linker

<400> SEQUENCE: 8

Gly Ser Ser Ser Ser Ser Ser Ser Ser Ser Ser Ser Ser Ser Ser
1               5                   10                  15

Gly
```

IMMUNOASSAY FOR THE DETERMINATION OF FC-REGION MODIFIED ANTIBODIES

CROSS-REFERENCE TO RELATED APPLICATIONS

This application is a continuation of, and claims priority to, International Patent Application No. PCT/EP2016/079086, filed on Nov. 29, 2016, which claims priority to European Patent Application No. 15197058.9, filed on Nov. 30, 2015. The entire contents of each of the above patent applications are hereby incorporated by reference.

SEQUENCE LISTING

The instant application contains a Sequence Listing submitted electronically in ASCII format and is hereby incorporated herein by reference in its entirety. Said ASCII copy, created May 15, 2018, is named P33227 USsequencelisting and is 12,288 bytes in size.

FIELD OF INVENTION

The current invention is in the field of immunoassays. Herein is reported a generic method for the determination of Fc-region modified antibodies in serum samples using a serial ELISA.

BACKGROUND OF THE INVENTION

For the improvement and optimization of pharmacokinetic parameters as well as of the effector function of therapeutic antibodies modifications of the molecular structure are introduced into a parent therapeutic antibody to generate variant antibodies. The modifications are not limited to the antigen recognition domains but also to the Fc-region.

For the detection and evaluation of Fc-region modified antibody variants a model system based on a non-biologically active antibody has been found. The non-biologically active antibody binds to an antigen that is not present in the experimental animal in which the evaluation of the Fc-region modification of the antibody is performed. It is a prerequisite for the detection that the used non-biologically active antibody does not cross-react with endogenous proteins of the experimental animal as well as with other components of the assay system. This can be achieved e.g. by using an antibody that binds to an artificial antigen, such as an anti-hapten antibody, e.g. an anti-digoxigenin antibody.

For the evaluation of the pharmacokinetic properties as well as for a proof of concept of a modification a detection method with suitable sensitivity as well as specificity is required. Further the detection method shall enable the detection of antibodies with different species-specific Fc-regions, such as e.g. human, cynomolgus, sheep or minipig Fc-region, but without interacting with the endogenous Immunoglobulin of the experimental animal.

In JP H01-223351 an assay for an antibody with a high specificity regardless of a difference in the type or the like of an animal used for production of the antibody to be assayed comprising immobilized and labelled antigen is reported.

In WO 96/22533 methods for immobilizing haptens on a test article are reported.

SUMMARY OF THE INVENTION

The method as reported herein is especially suited for antibodies comprising one or more mutations in the Fc-region, which influence the binding of/to anti-Fc-region antibodies generally used in generic detection methods.

The basic requirements for the ELISA to solve the current technical problem is that the analyte antibody has to be detected in a generic assay format independently of Fc-region modifications. This should also be applicable to the sample matrix. The assay should be as sensitive as possible in order to allow the determination of low concentration antibody samples.

It has been found that using a non-therapeutic antibody as surrogate to evaluate the in vivo pharmacokinetic properties associated with Fc-region variations allows for a non-interference assay setup. The surrogate antibody has a binding specificity directed to a non-endogenous target. The non-endogenous binding specificity is used in the detection assay for the interaction with the capture reagent and the detection reagent.

Thus, herein is reported a serial bridging ELISA for the in vitro determination of the amount of an Fc-region modified antibody in a serum sample obtained from a non-human experimental animal.

With the assay setup as reported herein, on which the method as reported herein is based, it is possible to
- to determine the amount of the Fc-region modified antibody without cross-reactivity to other serum/plasma components (of the experimental animal), i.e. the assay has a high specificity,
- generically determined the amount of the Fc-region modified antibody, i.e. the method is applicable independently of the species of the Fc-region and the experimental animal; this is valid for the analyte as well as for the sample matrix; this allows the detection of antibody Fc-region variants comprising different species specific Fc-regions in any experimental animal matrix,
- determine and confirm the structural integrity of the Fc-region modified antibody as well as the bivalency of the Fc-region modified antibody,
- determine the amount of the Fc-region modified antibody with high sensitivity and at a lower detection limit of at most 100 ng/mL,
- perform the method using standardized materials.

The antibody used in the method as reported herein is a surrogate antibody that specifically binds to a non-endogenous target. This ensures that in vivo no biological effect is exerted by the antibody and purely the pharmacokinetic properties associated with the Fc-region mutation/variation are evaluated.

The surrogate antibody used in the method as reported herein binds in one embodiment to a hapten. Haptens and anti-hapten antibodies are generally used in bioanalytical assays, such as ELISAs.

One aspect as reported herein is a method for the determination of the amount of a bivalent antibody in a serum or plasma sample obtained from a non-human experimental animal, whereby the antibody comprises one or more mutations in the Fc-region compared to the corresponding wild-type Fc-region that has a sequence of SEQ ID NO: 01, 02, or 03, wherein the method comprises the following steps in the following order:
  a) immobilizing a non-antibody polypeptide to which more than one copy of the antigen of the antibody is covalently conjugated on a solid surface, b) incubating the immobilized antigen with the sample to form an immobilized antigen-antibody complex,
c) incubating the immobilized antigen-antibody complex with the antigen conjugated to a detectable label to form an immobilized ternary complex,
d) determining the amount of the antibody by determining the amount of the detectable label in the immobilized ternary complex.

In one embodiment the bivalent antibody is a bivalent anti-hapten antibody.

In one embodiment the bivalent anti-hapten antibody is a bivalent anti-digoxygenin antibody.

One aspect as reported herein is a method for the determination of the amount of a bivalent anti-digoxygenin antibody in a serum or plasma sample obtained from a non-human experimental animal, whereby the antibody comprises one or more mutations in the Fc-region compared to the corresponding wild-type Fc-region that has a sequence of SEQ ID NO: 01, 02, or 03, wherein the method comprises the following steps in the following order:
a) immobilizing a non-antibody polypeptide to which more than one digoxygenin molecule is covalently conjugated on a solid surface,
b) incubating the immobilized non-antibody polypeptide to which more than one digoxygenin molecule is covalently conjugated with the sample to form an immobilized antigen-antibody complex,
c) incubating the immobilized antigen-antibody complex with digoxygenin conjugated to a detectable label to form an immobilized ternary complex,
d) determining the amount of the antibody by determining the amount of the detectable label in the immobilized ternary complex.

In one embodiment the non-antibody protein is a serum protein. In one embodiment the non-antibody polypeptide is bovine plasma albumin.

In one embodiment the one or more copies of the antigen of the antibody are chemically conjugated to the non-antibody polypeptide.

In one embodiment in the immobilizing step the concentration of the non-antibody polypeptide is about 50 ng/mL.

In one embodiment the antigen is conjugated to the detectable label via a specific binding pair. In one embodiment the specific binding pair (first component/second component) is selected from Streptavidin or Avidin/biotin, or antibody/antigen (see, for example, Hermanson, G. T., et al., Bioconjugate Techniques, Academic Press, 1996), or lectin/polysaccharide, or steroid/steroid binding protein, or hormone/hormone receptor, or enzyme/substrate, or IgG/Protein A and/or G.

In one embodiment the detectable label is an enzyme. In one embodiment the detectable label is a peroxidase. In one embodiment the detectable label is horseradish peroxidase. In one embodiment the concentration of the detectable label is about 300 mU/mL.

In one embodiment the determining is by incubating the immobilized ternary complex with 3,3',5,5'-tetramethyl benzidine.

One aspect as reported herein is the (use of a) method as reported herein for the determination of the pharmacokinetic properties (in-vivo half-life) of an antibody that has an Fc-region with mutations reducing the binding to Fc-receptors (Fcγ-receptor, FcRn) compared to a wild-type Fc-region of SEQ ID NO: 01, 02 or 03, wherein the method as reported herein is performed at at least two different points in time after the administration of said antibody to a non-human experimental animal (cynomolgus, mouse, rat, rabbit, minipig, guinea pig), and wherein from the results (plasma/serum sample concentration of said antibody at the at least two points in time after administration) the in-vivo half-life of said Fc-region/antibody is determined.

In one embodiment the at least two different points in time are 2, 3, 4, 5, 6, 7, 8, 9 or 10 points in time. In one preferred embodiment the at least two different points in time are 5 to 10 points in time. In one embodiment the points in time are 0.5 to 300 hours apart. In one embodiment the points in time are selected from the group consisting of 0.5 h, 6 h, 12 h, 24 h, 48 h, 72 h, 168 h, 336 h, 504 h and 672 h.

DETAILED DESCRIPTION OF THE INVENTION

Two main principles for bridging assay are known to a person skilled in the art which are exemplified in the following using the hapten digoxygenin and an anti-digoxigenin antibody as an example of a non-endogenous target and a non-endogenous target binding antibody.
1) capture using an anti-idiotypic antibody and a digoxigenylated antibody as detection reagent In this format a digoxigenylated antibody is used as primary detection reagent. But this can result in an interference: the anti-digoxygenin antibody as the analyte itself can also interact with digoxygenin of the detection reagent preventing the final detection of the analyte.
2) capture using an anti-Fc-region antibody In this format the analyte is captured by an anti-Fc-region antibody conjugated to a solid phase. Also in this format the analyte would compete with the digoxygenin-label of the detection antibody resulting in signal quenching. Further with this format no proof of the functional integrity of the analyte could be obtained. Also further this format is not species independent as on the one hand the capture antibody is species specific and on the other hand the capture antibody would cross-react with the endogenous antibodies of the experimental animal. Still further the assay would not be generically applicable for the detection of Fc-region modified antibody variants as the Fc-region modification could result in a loss of binding of the capture antibody.

I. Definitions

The term "about" denotes that the thereafter following value is no exact value but is the center point of a range that is +/−10% of the value, or +/−5% of the value, or +/−2% of the value, or +/−1% of the value. If the value is a relative value given in percentages the term "about" also denotes that the thereafter following value is no exact value but is the center point of a range that is +/−10% of the value, or +/−5% of the value, or +/−2% of the value, or +/−1% of the value, whereby the upper limit of the range cannot exceed a value of 100%.

The term "antibody" refers to a protein consisting of one or more polypeptide(s) substantially encoded by immunoglobulin genes. The recognized immunoglobulin genes include the different constant region genes as well as the myriad immunoglobulin variable region genes. Antibodies may exist in a variety of formats, including, for example, Fv, Fab, and F(ab)2 as well as single chains (scFv) or diabodies (e.g. Huston, J. S., et al., Proc. Natl. Acad. Sci. USA 85 (1988) 5879-5883; Bird, R. E., et al., Science 242 (1988) 423-426; in general, Hood et al., Immunology, Benjamin N.Y., 2nd edition (1984); and Hunkapiller, T. and Hood, L., Nature 323 (1986) 15-16).

An antibody in general comprises two so called light chain polypeptides (light chain) and two so called heavy chain polypeptides (heavy chain). Each of the heavy and light chain polypeptides contains a variable domain (variable region) (generally the amino terminal portion of the polypeptide chain) comprising binding regions that are able to interact with an antigen. Each of the heavy and light chain polypeptides comprises a constant region (generally the carboxyl terminal portion). The constant region of the heavy chain mediates the binding of the antibody i) to cells bearing a Fc gamma receptor (FcγR), such as phagocytic cells, or ii) to cells bearing the neonatal Fc receptor (FcRn) also known as Brambell receptor. It also mediates the binding to some factors including factors of the classical complement system such as component (C1q).

The variable domain of an antibody's light or heavy chain in turn comprises different segments, i.e. four framework regions (FR) and three hypervariable regions (CDR).

The term "drug antibody" according to the invention denotes an antibody which can be administered to an individual for the treatment of a disease. Within one assay performed according to the invention, the drug antibody and the capture antibody, or the drug antibody and the tracer antibody, respectively, comprise the "same" antibody molecule, e.g. recombinantly produced with the same expression vector and comprising the same amino acid sequence. Drug antibodies (therapeutic monoclonal antibodies) are being used widely for the treatment of various diseases such as oncological diseases (e.g. hematological and solid malignancies including non-Hodgkin's lymphoma, breast cancer, and colorectal cancer), immunological diseases, central nervous diseases, vascular diseases, or infectious diseases. Such antibodies are described, for example, by Levene, A. P., et al., Journal of the Royal Society of Medicine 98 (2005) 145-152. Such antibodies are, for instance, antibodies against CD20, CD22, HLA-DR, CD33, CD52, EGFR, G250, GD3, HER2, PSMA, CD56, VEGF, VEGF2, CEA, Levis Y antigen, IL-6 receptor, or IGF-1 receptor. Therapeutic antibodies are also described by Groner, B., et al., Curr. Mol. Meth. 4 (2004) 539-547; Harris, M., Lancet Oncol. 5 (2004) 292-302.

The term "monoclonal immunoglobulin" as used herein refers to an immunoglobulin obtained from a population of substantially homogeneous immunoglobulins, i.e. the individual immunoglobulins comprising the population are identical except for possible naturally occurring mutations that may be present in minor amounts. Monoclonal immunoglobulins are highly specific, being directed against a single antigenic site. Furthermore, in contrast to polyclonal immunoglobulin preparations, which include different immunoglobulins directed against different antigenic sites (determinants or epitopes), each monoclonal immunoglobulin is directed against a single antigenic site on the antigen. In addition to their specificity, the monoclonal immunoglobulins are advantageous in that they may be synthesized uncontaminated by other immunoglobulins. The modifier "monoclonal" indicates the character of the immunoglobulin as being obtained from a substantially homogeneous population of immunoglobulins and is not to be construed as requiring production of the immunoglobulin by any particular method.

The term "therapeutic antibody" relates to any antibody preparation which is intended for use in a human being. Preferably such therapeutic antibody will be a monoclonal antibody. Further preferred such monoclonal antibody will be obtained from a great ape or be a human monoclonal antibody or a humanized antibody. Preferably, it will be a human monoclonal antibody. Also preferred such therapeutic monoclonal antibody will be a humanized monoclonal antibody.

The term "target antigen" relates to a biomolecule which is bound by its corresponding therapeutic antibody. By way of example, the target antigen of a therapeutic antibody to HER2 (=ErbB2 or p 185 neu), like Herceptin® or Perjeta®, is HER2, of a therapeutic antibody to CD52, like Campath®, is CD52, of a therapeutic antibody to EGFR, like Erbitux®, is EGFR, of a therapeutic antibody to CD33, like Mylotarg®, is CD33, of a therapeutic antibody to Tag-72, like OncoScint®, is Tag-72, of a therapeutic antibody to 17-1A, like Panorex®, is 17-1A, of a therapeutic antibody to CD20, like Rituxan® or Zevalin®, is CD20, and of a therapeutic antibody to CD25, like Zenapax®, is CD25. The target antigen may either be a soluble, i.e. secreted or shed, target antigen or a cell-membrane bound target antigen.

The term "buffered" as used within this application denotes a solution in which changes of pH due to the addition or release of acidic or basic substances is leveled by a buffer substance. Any buffer substance resulting in such an effect can be used.

Preferably pharmaceutically acceptable buffer substances are used, such as e.g. phosphoric acid or salts thereof, acetic acid or salts thereof, citric acid or salts thereof, morpholine, 2-(N-morpholino) ethanesulfonic acid or salts thereof, histidine or salts thereof, glycine or salts thereof, or tris (hydroxymethyl) aminomethane (TRIS) or salts thereof. Especially preferred are phosphoric acid or salts thereof, or acetic acid or salts thereof, or citric acid or salts thereof, or histidine or salts thereof. Optionally the buffered solution may comprise an additional salt, such as e.g. sodium chloride, sodium sulphate, potassium chloride, potassium sulphate, sodium citrate, or potassium citrate.

The conjugation of a tracer and/or capture antibody to its conjugation partner can be performed by different methods, such as passive adsorption, chemical binding, or binding via a specific binding pair. The term "conjugation partner" as used herein denotes e.g. solid supports, polypeptides, detectable labels, members of specific binding pairs. In one embodiment the conjugation of the capture and/or tracer antibody to its conjugation partner is performed by chemically binding via N-terminal and/or ε-amino groups (lysine), ε-amino groups of different lysines, carboxy-, sulfhydryl-, hydroxyl-, and/or phenolic functional groups of the amino acid backbone of the antibody, and/or sugar alcohol groups of the carbohydrate structure of the antibody. In one embodiment the capture and/or tracer antibody are/is conjugated to its conjugation partner via a specific binding pair. Preferably the capture antibody is conjugated to biotin and immobilization to a solid support is performed via solid support immobilized avidin or streptavidin. Preferably the tracer antibody is conjugated to digoxigenin and linking to the detectable label is performed via an antibody against digoxigenin. The capture antibody is in another embodiment conjugated to the solid support by passive adsorption. An antibody conjugated to the solid support by passive adsorption comprises a mixture of antibodies conjugated to the solid support via different antibody sites. Thus, the capture antibody conjugated to the solid support is a mixture of two or more different conjugates wherein the conjugates differ in the antibody sites, i.e. the antibody residues, with which the conjugation to the solid support is effected. Passive adsorption is, e. g., described by Butler, J. E., in "Solid Phases in Immunoassay", page 205-225; Diamandis, E. P. and Christopoulos, T. K. (Editors): Immunoassays (1996) Academic Press San Diego.

Chromogens (fluorescent or luminescent groups and dyes), enzymes, NMR-active groups or metal particles, haptens, e.g. digoxigenin, are examples of "detectable labels". The detectable label can also be a photoactivatable crosslinking group, e.g. an azido or an azirine group. Metal chelates which can be detected by electrochemiluminescense are also preferred signal-emitting groups, with particular preference being given to ruthenium chelates, e.g. a ruthenium (bispyridyl)32+ chelate. Suitable ruthenium labeling groups are described, for example, in EP 0 580 979, WO 90/05301, WO 90/11511, and WO 92/14138. For direct detection the labeling group can be selected from any known detectable marker groups, such as dyes, luminescent labeling groups such as chemiluminescent groups, e.g. acridinium esters or dioxetanes, or fluorescent dyes, e.g. fluorescein, coumarin, rhodamine, oxazine, resorufin, cyanine and derivatives thereof. Other examples of labeling groups are luminescent metal complexes, such as ruthenium or europium complexes, enzymes, e.g. as used for ELISA or for CEDIA (Cloned Enzyme Donor Immunoassay, e.g. EP-A-0 061 888), and radioisotopes.

Indirect detection systems comprise, for example, that the detection reagent, e.g., the detection antibody is labeled with a first partner of a bioaffine binding pair. Examples of suitable binding pairs are hapten or antigen/antibody, biotin or biotin analogues such as aminobiotin, iminobiotin or desthiobiotin/avidin or Streptavidin, sugar/lectin, nucleic acid or nucleic acid analogue/complementary nucleic acid, and receptor/ligand, e.g., steroid hormone receptor/steroid hormone. Preferred first binding pair members comprise hapten, antigen and hormone. Especially preferred are haptens like digoxin and biotin and analogues thereof. The second partner of such binding pair, e.g. an antibody, Streptavidin, etc., usually is labeled to allow for direct detection, e.g., by the labels as mentioned above.

The "Fc-region" of an antibody is not involved directly in binding to the antibody's antigen, but exhibit various effector functions. Depending on the amino acid sequence of the constant region of the heavy chains, antibodies (immunoglobulins) are divided in the classes: IgA, IgD, IgE, IgG, and IgM. Some of these classes are further divided into subclasses (isotypes), i.e. IgG in IgG1, IgG2, IgG3, and IgG4, or IgA in IgA1 and IgA2. According to the immunoglobulin class to which an antibody belongs the heavy chain constant regions of immunoglobulins are called α (IgA), δ (IgD), ε (IgE), γ (IgG), and μ (IgM), respectively. The antibodies used in the methods as reported herein belong preferably to the IgG class. An "Fc-region of an antibody" is a term well known to the skilled artisan and defined on basis of the papain cleavage of antibodies. The antibodies in the methods as reported herein contain as Fc-region a human Fc-region or an Fc-region derived from human origin. In a further embodiment the Fc-region is either an Fc-region of a human antibody of the subclass IgG4 or an Fc-region of a human antibody of the subclass IgG1, IgG2, or IgG3. Pro238, Asp265, Asp270, Asn297 (loss of Fc-region carbohydrate), Pro329, Leu234, Leu235, Gly236, Gly237, Ile253, Ser254, Lys288, Thr307, Gln311, Asn434, or/and His435 are residues which, if altered, provide reduced Fcγ receptor binding (Shields, R. L., et al., J. Biol. Chem. 276 (2001) 6591-6604; Lund, J., et al., FASEB J. 9 (1995) 115-119; Morgan, A., et al., Immunology 86 (1995) 319-324; EP 0 307 434). Exemplary antibodies that can be used in the methods as reported herein are in regard to Fcγ receptor binding of IgG4 subclass or of IgG 1 or IgG2 subclass, with a mutation in L234, L235, and/or D265, and/or contains the PVA236 mutation, with the mutations S228P, L234A, L235A, L235E, and/or PVA236 (PVA236 means that the amino acid sequence ELLG (given in one letter amino acid code) from amino acid position 233 to 236 of IgG1 or EFLG of IgG4 is replaced by PVA), with the mutations S228P of IgG4, and L234A and L235A of IgG1. The Fc-region of an antibody is directly involved in ADCC (antibody-dependent cell-mediated cytotoxicity) and CDC (complement-dependent cytotoxicity). An antibody which does not bind Fcγ receptor and/or complement factor C1q does not elicit antibody-dependent cellular cytotoxicity (ADCC) and/or complement dependent cytotoxicity (CDC).

As used herein the term "Fc-region derived from human origin" denotes an Fc-region which is either an Fc-region of a human antibody of the subclass IgG4 or an Fc-region of a human antibody of the subclass IgG 1, IgG2, or IgG3, including mutated forms thereof. An "Fc-region of an antibody" is a term well known to the skilled artisan and defined on the basis of papain cleavage of antibodies.

The term "linker" or "peptidic linker" as used within this application denotes peptide linkers of natural and/or synthetic origin. They consist of a linear amino acid chain wherein the 20 naturally occurring amino acids are the monomeric building blocks. The chain has a length of from 1 to 50 amino acids, preferred between 1 and 28 amino acids, especially preferred between 3 and 25 amino acids. The linker may contain repetitive amino acid sequences or sequences of naturally occurring polypeptides, such as polypeptides with a hinge-function. The linker has the function to ensure that a peptide conjugated to an anti-CD4 antibody can perform its biological activity by allowing the peptide to fold correctly and to be presented properly. Preferably the linker is a "synthetic peptidic linker" that is designated to be rich in glycine, glutamine, and/or serine residues. These residues are arranged e.g. in small repetitive units of up to five amino acids, such as GGGS (SEQ ID NO: 04), GGGGS (SEQ ID NO: 05), QQQQG (SEQ ID NO: 06), or SSSSG (SEQ ID NO: 07). This small repetitive unit may be repeated for two to five times to form a multimeric unit. At the amino- and/or carboxy-terminal ends of the multimeric unit up to six additional arbitrary, naturally occurring amino acids may be added. Other synthetic peptidic linkers are composed of a single amino acid, that is repeated between 10 to 20 times and may comprise at the amino- and/or carboxy-terminal end up to six additional arbitrary, naturally occurring amino acids, such as e.g. serine in the linker GSSSSSSSSSSSSSSSG (SEQ ID NO: 08). All peptidic linkers can be encoded by a nucleic acid molecule and therefore can be recombinantly expressed. As the linkers are themselves peptides, the antifusogenic peptide is connected to the linker via a peptide bond that is formed between two amino acids.

Methods and techniques known to a person skilled in the art, which are useful for carrying out the current invention, are described e.g. in Ausubel, F. M., ed., Current Protocols in Molecular Biology, Volumes I to III (1997), Wiley and Sons; Sambrook et al., Molecular Cloning: A Laboratory Manual, Second Edition, Cold Spring Harbor Laboratory Press, Cold Spring Harbor, N.Y. (1989).

A "polypeptide" is a polymer consisting of amino acids joined by peptide bonds, whether produced naturally or synthetically. Polypeptides of less than about 20 amino acid residues may be referred to as "peptides", whereas molecules consisting of two or more polypeptides or comprising one polypeptide of more than 100 amino acid residues may be referred to as "proteins". A polypeptide may also comprise non-amino acid components, such as carbohydrate groups, metal ions, or carboxylic acid esters. The non-amino acid components may be added by the cell, in which the polypeptide is expressed, and may vary with the type of cell. Polypeptides are defined herein in terms of their amino acid backbone structure or the nucleic acid encoding the same. Additions such as carbohydrate groups are generally not specified, but may be present nonetheless.

The term "sample" includes, but is not limited to, any quantity of a substance from a living thing or formerly living thing. Such living things include, but are not limited to, humans, mice, monkeys, rats, rabbits, and other animals. In one embodiment the sample is obtained from a monkey, especially a cynomolgus monkey, or a rabbit, or a mouse or rat. Such substances include, but are not limited to, in one embodiment whole blood, serum, or plasma from an individual, which are the most widely used sources of sample in clinical routine.

A "solid phase" denotes a non-fluid substance, and includes particles (including microparticles and beads) made from materials such as polymer, metal (paramagnetic, ferromagnetic particles), glass, and ceramic; gel substances such as silica, alumina, and polymer gels; capillaries, which may be made of polymer, metal, glass, and/or ceramic; zeolites and other porous substances; electrodes; microtiter plates; solid strips; and cuvettes, tubes or other spectrometer sample containers. A solid phase component of an assay is distinguished from inert solid surfaces with which the assay may be in contact in that a "solid support" contains at least one moiety on its surface, which is intended to interact chemically with a molecule. A solid phase may be a stationary component, such as a chip, tube, strip, cuvette, or microtiter plate, or may be a non-stationary components, such as beads and microparticles. Microparticles can also be used as a solid support for homogeneous assay formats. A variety of microparticles that allow both non-covalent or covalent attachment of proteins and other substances may be used. Such particles include polymer particles such as polystyrene and poly(methylmethacrylate); gold particles such as gold nanoparticles and gold colloids; and ceramic particles such as silica, glass, and metal oxide particles. See for example Martin, C. R., et al., Analytical Chemistry-News & Features, May 1 (1998) 322A-327A, which is incorporated herein by reference. The solid phase may optionally be coated, entirely or in certain areas. On the surface of the material any array of spots or an area is present, either visible or in coordinates. On each spot or the area, respectively, a polypeptide, with or without linker or spacer to the surface of the material, may be immobilized. Preferably the immobilized polypeptide is a receptor according to the current invention capable of binding Fc-region of an IgG. Solid phases for immunoassays according to the invention are widely described in the state of the art (see, e.g., Butler, J. E., Methods 22 (2000) 4-23).

The term "standard" or "standard substance" which can be used interchangeably within this application denotes a point of reference for an analytical method and is used to set up a value against which other results of the same analytical method are compared. The term "positive control" as used herein denotes a standard substance with which, if employed in an analytical method, a response above a defined cut-off or threshold value will be achieved. The cut off value is in general the average value obtained in the analysis of samples not containing anti-drug antibodies plus two times, preferably three times, the standard deviation of the values.

II. The Method as Reported Herein

It has now been found that with the method as reported herein the drawbacks of the prior art methods for the determination of the amount of an Fc-region modified antibody in a serum or plasma sample obtained from a non-human experimental animal can be circumvented as well as all required specificities for the detection method can be fulfilled.

It has been found that using non-antibody based capture and detection reagents is advantageous.

It has been found that by using a biotinylated RPLA-digoxygenin conjugate an improved signal to noise ratio e.g. of 32.8 compared to 9.5 for a directly biotinylated digoxygenin, can be obtained. The RPLA based capture reagent comprises each more than one biotin as well as digoxygenin molecule resulting in a signal increase. With doubly derivatized RPLA (e.g. biotinylated and digoxigenylated) a directed immobilization of the RPLA is possible.

It has been found that a serial sequence of steps in contrast to pre-incubation of the reagents results in an increased sensitivity (improvement of about factor 2). The method as reported herein has a useable determination range of from 1.56 ng/mL (lower limit of detection) to 200 ng/mL when using ABTS as enzymatic substrate. Additionally it has been found that the pre-incubation of analyte and detection reagent results in a hook-effect. Further the pre-incubation results especially at high concentrations of the detection reagent (digoxigenylated peroxidase) in a reduction of the assay signal in some cases even in the total suppression of the signal.

It has been found that for the serial assay setup coating densities of 50 ng/mL or less double derivatized RPLA are advantageous in order to avoid avidity effects.

In summary the serial assay setup has the advantages of a low number of interferences and a high sensitivity compared to the pre-incubation setup.

It has further been found that by using TMB as chromogenic substrate compared to the use of ABTS as chromogenic substrate the sensitivity of the assay can be further improved (down to 0.94 ng/mL). This results in a useable range of from 35 ng/mL to 0.55 ng/mL.

The standard curves obtained in different matrices are comparable with a coefficient of variation of at most 5%.

It has been found by analyzing multiple different antibodies with plasma concentrations of up to 100 μg/mL that the assay as reported herein shows no cross-reactivity and selectively detects the analyte (anti-digoxygenin antibody). Further the plasma of different animals showed no interference.

The capture reagent used in the method as reported herein is not an antibody or derived from an antibody and, thus, does not have directed binding specificities. It has the functionalities of a dual domain presenting scaffold: one domain is for the immobilization to the solid phase and one domain is the antigen of the antibody to be determined.

The capture reagent used in the method as reported herein is a conjugate of the antibody of the antibody to be detected and a detectable label. The conjugation can be performed either directly via functional groups on the antigen and the detectable label or via a linker.

By using reagents as outlined above the method as reported herein requires fewer reagents.

In the method as reported herein the analyte forms an immunocomplex with the capture and detection reagent without the need of a secondary detection reagent. Additionally by using this assay format a generic detection as well as the determination of the structural integrity of the analyte is possible.

In one embodiment the antibody is an antibody of the IgG class.

In one embodiment the antibody is an anti-hapten antibody. In one embodiment the antibody selected from the group consisting of an anti-biotin antibody, an anti-digoxygenin antibody, an anti-theophylline antibody, an anti-helicar antibody, and an anti-bromodeoxyuridine antibody.

In one embodiment the antibody is an anti-digoxygenin antibody.

As the immunoassay uses the binding specificities of the CDRs of the analyte an independence from the framework regions, the Fc-region and the species from which the antibody is derived can be achieved. Thus, the assay as reported herein is only depending on the binding specificity of the antibody. Therefore the assay as reported herein is a generic assay with respect to the species from which the Fc-region of the antibody is derived and the experimental animal from which the sample is obtained.

In the detection method as reported herein the recognition of the antibody's antigen is independent of the conjugation state of the antigen but depends on the binding strength of the antibody to its antigen.

In one embodiment the capture reagent, i.e. the antigen, is conjugated to a solid phase. In one embodiment the conjugation to the solid phase is via biotinylated bovine plasma albumin (RPLA).

Bovine plasma albumin (RPLA) is a 66 kDa protein globular protein obtained from bovine plasma.

For the pharmacological and toxicological evaluation of novel therapeutics often primates, dogs or minipig are used as non-rodent species.

A potential source of errors in the analysis of blood samples resides in the sample matrix. For example proteins present in the matrix can interact non-specifically with the capture and tracer reagents.

One aspect as reported herein is a method for the determination of the amount of a bivalent antibody in a serum or plasma sample obtained from a non-human experimental animal, whereby the antibody comprises one or more mutations in the Fc-region compared to the corresponding wild-type Fc-region that has a sequence of SEQ ID NO: 01, 02, or 03, wherein the method comprises the following steps in the following order:
  a) immobilizing biotinylated bovine plasma albumin to which more than one copy of the antigen of the antibody is covalently conjugated on a solid avidin or streptavidin coated surface, preferably at a concentration of 50 ng/ml,
  a1) optionally a wash step,
  b) incubating the immobilized antigen with the sample to form an immobilized antigen-antibody complex, preferably the antibody has a concentration of from 0.55 ng/ml to 35 ng/ml, further preferably the sample comprises 10% serum,
  b1) optionally a wash step,
  c) incubating the immobilized antigen-antibody complex with the antigen conjugated to a detectable label to form an immobilized ternary complex, preferably the detectable label is peroxidase, further preferably the peroxidase is used at a concentration of 300 mU/ml,
  c1) optionally a wash step,
  d) determining the amount of the antibody by determining the amount of the detectable label in the immobilized ternary complex.

Polypeptides (i.e. the antigen) and antibodies contain a number of reactive moieties, such as, for example, amino groups (lysins, alpha-amino groups), thiol groups (cystins, cysteine, and methionine), carboxylic acid groups (aspartic acid, glutamic acid) and sugar-alcoholic groups. These can be employed for coupling to a binding partner like a surface, a protein, a polymer (such as e.g. PEG, Cellulose or Polystyrol), an enzyme, or a member of a binding pair (see e.g. Aslam M. and Dent, A., Bioconjuation MacMillan Ref. Ltd. (1999) 50-100).

One of the most common reactive groups of proteins is the aliphatic ε-amine of the amino acid lysine. In general, nearly all antibodies contain abundant lysine residues. Lysine amines/amino groups are reasonably good nucleophiles above pH 8.0 (pKa=9.18) and therefore react easily and cleanly with a variety of reagents to form stable bonds.

Another common reactive group in antibodies is the thiol residue from the sulfur-containing amino acid cystine and its reduction product cysteine (or half cystine). Cysteine contains a free thiol group, which is more nucleophilic than amines and is generally the most reactive functional group in a protein. Thiols are generally reactive at neutral pH, and therefore can be coupled to other molecules selectively in the presence of amines. Since free sulfhydryl groups are relatively reactive, proteins with these groups often exist with them in their oxidized form as disulfide groups or disulfide bonds.

In addition to cystine and cysteine, some proteins also have the amino acid methionine, which is containing sulfur in a thioether linkage. The literature reports the use of several thiolating crosslinking reagents such as Traut's reagent (2-iminothiolane), succinimidyl (acetylthio) acetate (SATA), or sulfosuccinimidyl 6-[3-(2-pyridyldithio) propionamido] hexanoate (Sulfo-LC-SPDP) to provide efficient ways of introducing multiple sulfhydryl groups via reactive amino groups.

Reactive esters, particularly N-hydroxysuccinimide (NHS) esters, are among the most commonly employed reagents for modification of amine groups. The optimum pH for reaction in an aqueous environment is pH 8.0 to 9.0.

Isothiocyanates are amine-modification reagents and form thiourea bonds with proteins. They react with protein amines in aqueous solution (optimally at pH 9.0 to 9.5).

Aldehydes react under mild aqueous conditions with aliphatic and aromatic amines, hydrazines, and hydrazides to form an imine intermediate (Schiff's base). A Schiff's base can be selectively reduced with mild or strong reducing agents (such as sodium borohydride or sodium cyanoborohydride) to derive a stable alkyl amine bond.

Other reagents that have been used to modify amines are acid anhydrides. For example, diethylenetriaminepentaacetic anhydride (DTPA) is a bifunctional chelating agent that contains two amine-reactive anhydride groups. It can react with N-terminal and ε-amine groups of proteins to form amide linkages. The anhydride rings open to create multivalent, metal-chelating arms able to bind tightly to metals in a coordination complex.

The principles of different immunoassays are described, for example, by Hage, D. S. (Anal. Chem. 71 (1999) 294R-304R). Lu, B., et al. (Analyst 121 (1996) 29R-32R) report the orientated immobilization of antibodies for the use in immunoassays. Avidin-biotin-mediated immunoassays are reported, for example, by Wilchek, M., and Bayer, E. A., in Methods Enzymol. 184 (1990) 467-469.

Figure 1:
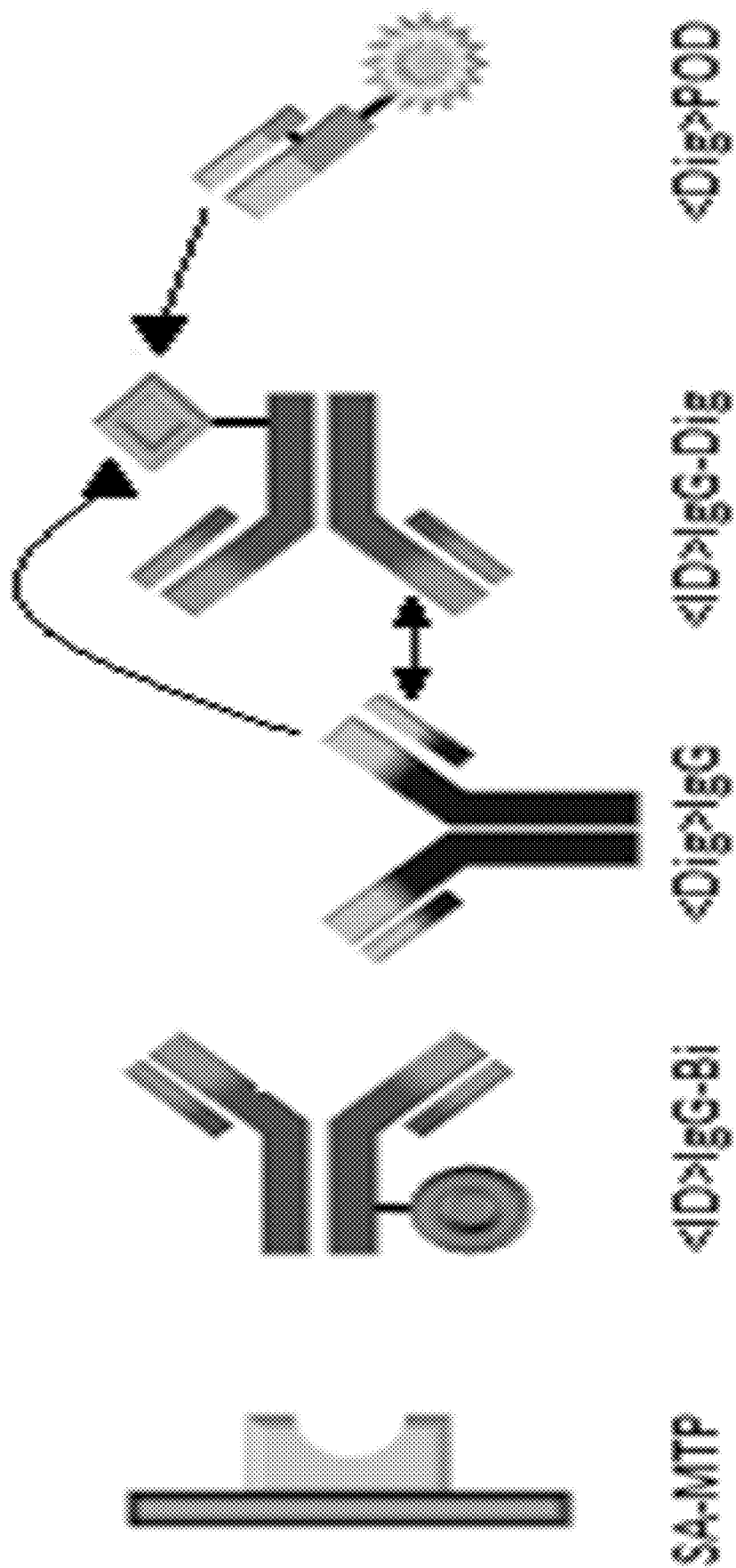
FIG. 1 Scheme of a standard immunoassay.
Figure 2:
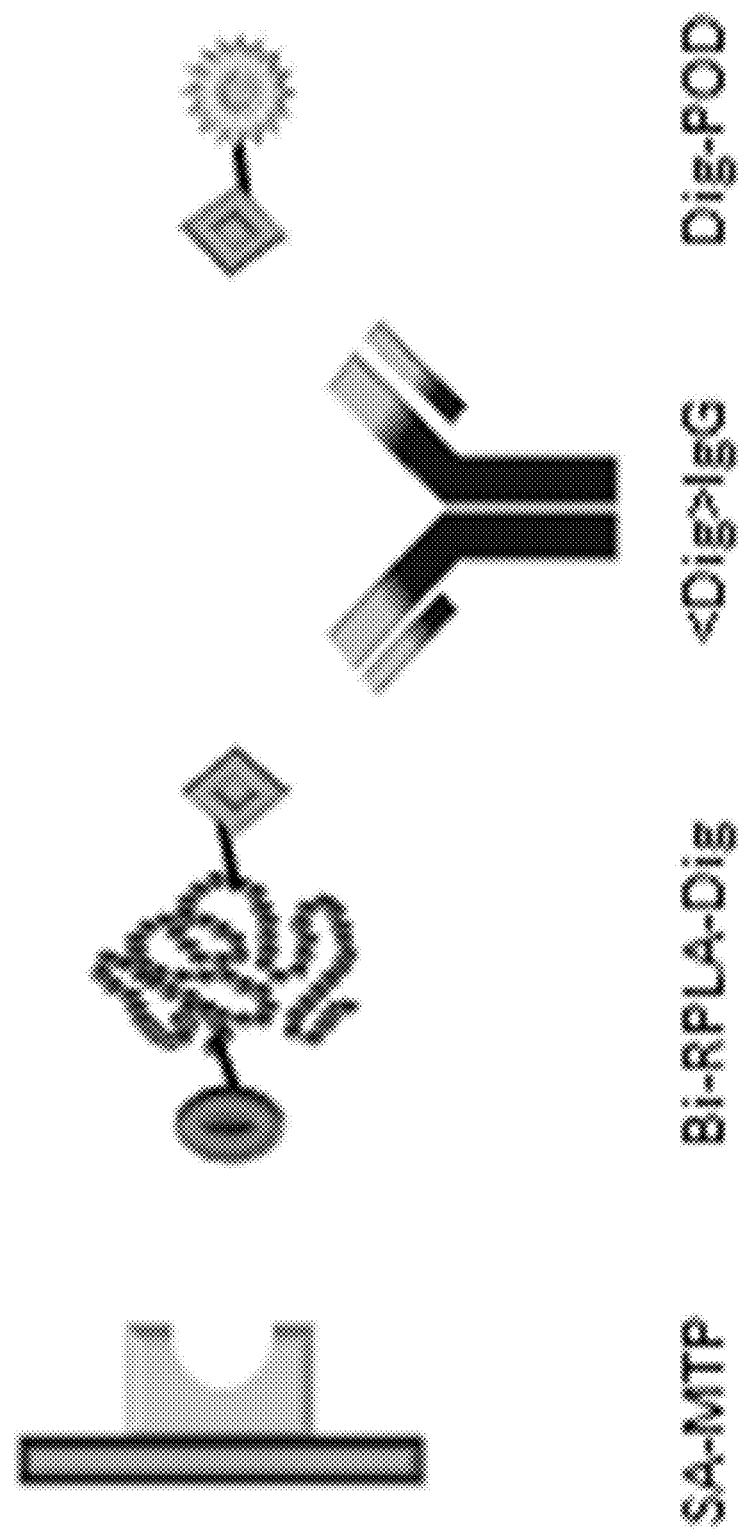
FIG. 2 Scheme of the immunoassay as reported herein.

The following examples, figures and sequences are provided to aid the understanding of the present invention, the true scope of which is set forth in the appended claims. It is understood that modifications can be made in the procedures set forth without departing from the spirit of the invention.

Materials

| Device | Type | Manufacturer |
|---|---|---|
| fluorescence spectrometer | Infinite F200 PRO | Tecan Group AG |
| SPR | BIAcore T100 | GE Healthcare |
| photometer | Sunrise | Tecan Austria GmbH |
| pipettes | 1-, 8-, 12-channel pipettes | Eppendorf AG |
| shaker | Thermo-Shaker PHMP-4 | Grant-bio |
| washer | hydroFlex | Tecan Austria GmbH |
| centrifuge | Galaxy Mini | VWR International |

| Type | Manufacturer |
|---|---|
| BIAcore T100 control | GE Healthcare |
| i-control 1.10 | Tecan Group AG |
| Microsoft Office 2010 | Microsoft |
| WinNonline 5.3 | Pharsight |
| XLfit4 | IDBS |
| ChemSketch 12.0 | Advanced Chemistry Development Inc. |
| 10× PBS | Roche Diagnostics GmbH |
| ABTS Solution | Roche Diagnostics GmbH |
| Beagle-poolserum | Bioreclamation LLC. |
| Bi(XOSu)-RPLA-Dig(XOSu) | Roche Diagnostics GmbH |
| BM Blue POD Substrate (TMB) | Roche Diagnostics GmbH |
| Bronidox (=5-Bromo-5-nitro-1,3-dioxane) | Sigma Aldrich |
| Cynomolgus-poolserum | Sera Laboratories International Ltd |
| Dig-3-CME-UEEK-Bi | Roche Diagnostics GmbH |
| Dig(XOSu)-POD | Roche Diagnostics GmbH |
| HPPA | Sigma-Aldrich |
| Human-poolserum (n = 20; 10 female, 10 male) | Trina Bioreactives AG |
| mAk<Dig>H-IgG LALA | Roche Diagnostics GmbH |
| mAk<Dig>H-IgG LALA PG | Roche Diagnostics GmbH |
| mAk<Dig>H-IgG LALA PG AAA | Roche Diagnostics GmbH |
| mAk<Dig>H-IgG wt | Roche Diagnostics GmbH |
| mAk<Dig>M-19.11.-IgG | Roche Diagnostics GmbH |
| mouse-poolserum | Roche Diagnostics GmbH |
| Minipig-Individual plasma | F. Hoffmann-La Roche AG |
| Minipig-poolplasma | Roche Diagnostics GmbH |
| pAk<Dig>S-Fab-POD | Roche Diagnostics GmbH |
| pAk<M-Fc>Rb-IgG-HRP | Jackson Immuno Research Laboratories INC. |
| Polystyrol-MTP Maxisorb | Thermo Fisher Scientific Inc./NUNC |
| RPLA-Dig(XOSu) | Roche Diagnostics GmbH |
| Streptavidin-coated MTP | MicroCoat |
| Streptavidin-coated MTP C96 white | Greiner Bio-One GmbH |
| Streptavidin-POD conjugate | Roche Diagnostics GmbH |
| Tween 20 | Calbiochem |
| non-coated pre-incubation-MTP (polypropylene) | Thermo Fisher Scientific Inc./NUNC |
| ELISA universal buffer | Roche Diagnostics GmbH |
| hydrogen peroxide 30% | Merck KgaA |

| Type | Composition |
|---|---|
| Assay-buffer | Universal buffer for ELISA |
| Coating-buffer | 0.1M $NaHCO_3$, pH 9.6 |
| Blocking-buffer | 1× PBS, 5% RPLA1, Bronidox 0.002% |
| stopping buffer | 0.5M $H_2SO_4$ |
| TRIS-buffer | 12.14 g Tris + 3.5 ml HCL (ad 1l), pH 8.6 |
| Universal buffer | — |
| Wash buffer | 1× PBS, 0.05% Tween 20, 0.002% Bronidox |

Example 1

Immunoassay

The method as reported herein is a non-competitive enzyme linked immunosorbent assay in sandwich format. This assay setup allows for the detection of non-biologically active antibodies in 10% matrix (serum).

A streptavidin-coated 96-well plate (SA-MTP) was coated with activated biotin (biotin-(XOSu)-RPLA-digoxigenin(XOSu) (BI-RPLA-DIG). The coating was done with 100 µL of a solution (50 ng/mL BI-RPLA-DIG) added to each well for one hour at room temperature with shaking (500 rpm). Thereafter the wells are washed three times with 300 µL wash buffer each.

For analysis standard samples, quality control samples and samples were analyzed in duplicates. Standard samples and quality control samples were prepared in 100% matrix and diluted afterwards 1:10 (v/v) with assay buffer. The standard samples were prepared using the same material also applied to the experimental animal in a 1:1 dilution series in 100% matrix as follows: The first standard sample (STD A) was prepared using a monoclonal murine anti-digoxigenin antibody (mAb<Dig>M-19.11-IgG) at a concentration of 350 ng/mL in 100% matrix. By diluting STD A with 100% matrix STD B was obtained and so on up to STD G (350 ng/mL—5.5 ng/mL). The eighth standard is non-spiked 100% matrix. The standard samples and the blank were diluted 1:10 (v/v) with assay buffer. Each sample and standard was added in a volume of 100 µL to the wells. The plate was incubated for one hour at room temperature with shaking (500 rpm). Thereafter the supernatant was removed and the wells were washed three times with 300 µL per well wash buffer. To each well 100 µL of the detection solution (digoxygenin(XOSu)-peroxidase (DIG_POD); 300 mU/mL) was added. Thereafter the plate was incubated for one hour at room temperature with shaking (500 rpm). After removal of the supernatant each well was washed three times with 300 µL was buffer each. The color reaction was initiated by addition of 100 µL of a 3,3',5,5'-tetramethyl benzidine (TMB) solution. After 18 minutes the reaction was stopped by the addition of 0.5 mol/L phosphoric acid and extinction determined at 450 nm with a reference value taken at 690 nm.

Example 2

Capture Reagent
1) Non-Specific Adsorption

The capture reagent digoxygenin-conjugated bovine plasma albumin (RPLA-DIG) was used in this example.

A solution comprising 1.5 µg/mL RPLA-DIG in 100 mM sodium hydrogen carbonate buffer (pH 9.6) was prepared. Each well of a polystyrol multi-well plate was filled with 200 µL of this solution and incubated for one hour with shaking. Thereafter the supernatant was removed and the wells were washed three times each with 300 µL/well blocking buffer comprising bovine serum albumin. After removal of the supernatant the wells are washed three times each.

Standard samples were prepared using a 1:1 dilution series in 100% assay buffer as follows: The first standard sample (STD A) was prepared using a monoclonal murine anti-digoxigenin antibody (mAb<Dig>M-19.11-IgG) at a concentration of 100 ng/mL in assay buffer. By diluting STD A with assay buffer 1:1 (100% dilution) STD B was obtained and so on up to STD G. The eighth standard is non-spiked assay buffer.

Six standard series in duplicate were determined (incubation time in the well one hour).

For detection a solution comprising a horseradish peroxidase conjugated rabbit polyclonal anti-Fc-antibody (pAk<M-Fc>Rb-IgG-HRP) was prepared (50 mU/mL). This detection solution is diluted to 25 mU/mL, 12.5 mU/mL, 6.25 mU/ml, 3.13 mU/mL and 1.56 mU/mL so that six detection solutions with different detection reagent concentrations were obtained.

After removing the supernatant from the wells and three-time washing the detection reagent is added to the wells. Therefore for each of the six standard series 100 µL of the respective dilution of the detection reagent is added. After the incubation the supernatant is removed and an ABTS solution is added. The produced colored reaction product is determined at 405 nm with a reference wavelength of 490 nm.

| | POD-conc. [mU/ml] | | | | | | | | | | |
|---|---|---|---|---|---|---|---|---|---|---|---|
| | 50 | | 25 | | 12.5 | | 6.25 | | 3.13 | | 1.56 |
| | t [min] | | | | | | | | | | |
| | 4.83 | | 8.97 | | 17.25 | | 35.18 | | 57.95 | | 57.95 |
| STD [ng/ml] | Ext. [OD] | CV [%] | Ext. [OD] | CV [%] | Ext. [OD] | CV [%] | Ext. [OD] | CV [%] | Ext. [OD] | CV [%] | Ext. [OD] | CV [%] |
| 100 | 2.406 | 1 | 2.419 | 0 | 2.451 | 2 | 2.386 | 3 | 1.896 | 2 | 1.037 | 2 |
| 50.0 | 2.085 | 1 | 2.035 | 1 | 2.025 | 1 | 2.033 | 1 | 1.609 | 1 | 0.867 | 0 |
| 25.0 | 1.768 | 2 | 1.637 | 0 | 1.597 | 1 | 1.599 | 1 | 1.218 | 0 | 0.650 | 0 |
| 12.5 | 1.247 | 2 | 1.093 | 0 | 1.058 | 1 | 1.070 | 1 | 0.789 | 3 | 0.424 | 2 |
| 6.25 | 0.780 | 2 | 0.647 | 0 | 0.621 | 2 | 0.636 | 1 | 0.466 | 4 | 0.259 | 6 |
| 3.13 | 0.437 | 0 | 0.362 | 2 | 0.346 | 5 | 0.350 | 4 | 0.267 | 2 | 0.149 | 0 |
| 1.56 | 0.232 | 1 | 0.195 | 1 | 0.186 | 3 | 0.197 | 1 | 0.152 | 2 | 0.093 | 3 |
| 0 | 0.021 | 3 | 0.022 | 3 | 0.025 | 3 | 0.032 | 0 | 0.037 | 0 | 0.038 | 2 |
| S:N | 102 | | 95 | | 83 | | 64 | | 43 | | 23 | |

2) Specific Adsorption

Two different capture reagents for specific and directed adsorption were prepared: i) with defined BI-DIG stoichiometry: DIG-3-CME-UEEK-Bi (DIG=digoxygenin; 3-CME=3-carboxymethyl ether; UEEK=β-alanine-glutamic acid-glutamic acid-lysine; BI=biotin; MW approx. 1.1 kDa); denoted as BI-DIG in the following) ii) with undefined BI-DIG stoichiometry: BI-RPLA-DIG (RPLA=bovine plasma albumin; MW approx. 70 kDa).

As standard sample an anti-ANG2 antibody has been used in this example.

The capture reagents were each incubated over night with the standard and first detection reagent (see previous example) incubated. The incubation is performed in polypropylene plates in which no non-specific adsorption to the surface occurs.

For detection a digoxigenylated anti-idiotypic antibody is added to the overnight pre-incubated sample (mAb<ID-mAb<ANG2>>M.2.6.81-IgG(SPA)-Dig(XOSu) (DIG-IGG)). The signal was developed using a peroxidase conjugate polyclonal anti-digoxygenin antibody (pAk<DIG>S-Fab-POD).

The capture reagent BI-DIG was used at a concentration of 219.99 ng/mL and the capture reagent BI-RPLA-DIG was used at a concentration of 14 μg/mL. With this concentrations the capture reagents were present during the pre-incubation in a 100-fold molar excess (BI-100) compared to the other reagents. In a 1:10 (BI-10) and 1:100 dilution (BI-1) solutions with a 1:10 and 1:1 molar ratio were obtained. Analogously the first detection reagent was used at a concentration of 30 μg/mL (DIG-100) resulting in a molar ratio of capture reagent to detection reagent of 1:100. In a 1:10 (DIG-10) and 1:100 dilution (DIG-1) solutions with a 1:10 and 1:1 molar ratio were obtained. The analyte was employed at a concentration of 3 μg/mL (STD-10). A 1:10 dilution provided STD-1.

The pre-generated immune complex containing solution was applied to the wells of a streptavidin-coated multi-well plate and the secondary detection reagent against the Fc-region of the analyte (pAb<M-Fc>Rb-IGG-HRP; HRP=horseradish peroxidase) was added in a concentration of 160 ng/mL. After an incubation time of one hour the substrate solution was added and the generated colored reaction product determined photometrically.

The results for the BI-DIG conjugate determined at 18.5 min are shown in the following table.

|  | DIG-0 | | | DIG-10 | | |
| --- | --- | --- | --- | --- | --- | --- |
|  | STD-0 | STD-1 | STD-10 | STD-0 | STD-1 | STD-10 |
| BI-0 | 0.025 | 0.026 | 0.026 | 0.060 | 0.043 | 0.027 |
| BI-1 | 0.023 | 0.025 | 0.024 | 0.046 | 0.039 | 0.036 |
| BI-10 | 0.023 | 0.027 | 0.029 | 0.043 | 0.036 | 0.376 |
| BI-100 | 0.024 | 0.028 | 0.035 | 0.042 | 0.035 | 0.399 |
| BI-0 | 0.024 | 0.025 | 0.025 | 0.223 | 0.221 | 0.112 |
| BI-1 | 0.025 | 0.025 | 0.029 | 0.217 | 0.213 | 0.122 |
| BI-10 | 0.025 | 0.036 | 0.144 | 0.236 | 0.218 | 0.140 |
| BI-100 | 0.028 | 0.032 | 0.246 | 0.257 | 0.226 | 0.172 |
|  | DIG-1 | | | DIG-100 | | |

The results for the BI-RPLA-DIG conjugate determined at 18.5 min are shown in the following table.

|  | DIG-0 | | | DIG-10 | | |
| --- | --- | --- | --- | --- | --- | --- |
|  | STD-0 | STD-1 | STD-10 | STD-0 | STD-1 | STD-10 |
| BI-0 | 0.030 | 0.029 | 0.030 | 0.070 | 0.060 | 0.036 |
| BI-1 | 0.027 | 0.033 | 0.032 | 0.051 | 0.057 | 1.565 |
| BI-10 | 0.027 | 0.032 | 0.041 | 0.054 | 0.063 | 1.754 |
| BI-100 | 0.028 | 0.032 | 0.037 | 0.056 | 0.057 | 0.086 |
| BI-0 | 0.030 | 0.029 | 0.032 | 0.254 | 0.287 | 0.213 |
| BI-1 | 0.029 | 0.118 | 0.424 | 0.261 | 0.261 | 0.225 |
| BI-10 | 0.029 | 0.041 | 0.962 | 0.301 | 0.332 | 0.362 |
| BI-100 | 0.033 | 0.035 | 0.042 | 0.469 | 0.465 | 0.523 |
|  | DIG-1 | | | DIG-100 | | |

It can be seen that only for high concentrations the digoxigenylated antibody binds non-specifically to the plate. It can further be seen that the extinction maximum for both capture reagents is in the same molar ratio. In case of the BI-DIG is the molar ratio of the capture reagent is shifted by a factor of 10 up compared to the BI-RPLA-DIG. The direct comparison of the signal-to-noise ratio (S/N) of the extinction maximum shows that for the Bi-RPLA-Dig the S/N is 32.8 (S/N=1.754/0.054), whereas for the BI-DIG is 9.5 (S/N=0.399/0.042).

Example 3

Assay-Setup

Different variants of assay setups are compared in this example: i) serial setup (application of capture reagent, analyte and detection reagent, each step is separated by one washing step), ii) pre-incubation of analyte and detection reagent, and iii) pre-incubation of capture reagent, analyte and detection reagent.

1) Serial Setup

The results obtained with the serial setup after 18.6 min are shown in the following table. The maximum of 36.3 has been obtained with an analyte concentration of 50 ng/mL.

| c(Bi-RPLA-Dig) [ng/mL] | c(Dig-POD) [mU/mL] | | | | | |
| --- | --- | --- | --- | --- | --- | --- |
|  | 25 | 50 | 75 | 100 | 150 | 300 |
|  | S:N (at 50 ng/ml analyte) | | | | | |
| 400 | 5.1 | 5.9 | 6.0 | 6.5 | 6.7 | 8.1 |
| 200 | 9.9 | 11.4 | 11.9 | 12.9 | 13.8 | 16.4 |
| 100 | 17.7 | 19.4 | 19.7 | 21.3 | 22.4 | 25.1 |
| 75 | 22.6 | 25.5 | 25.6 | 27.2 | 26.7 | 32.4 |
| 50 | 25.8 | 30.2 | 28.7 | 30.5 | 31.0 | 36.3 |
| 25 | 25.7 | 29.0 | 28.4 | 29.5 | 32.2 | 35.3 |
| 10 | 16.3 | 20.2 | 18.8 | 18.6 | 19.9 | 20.4 |
| 5 | 8.8 | 10.3 | 9.6 | 9.4 | 11.4 | 11.3 |

It can be seen that with decreasing BI-RPLA-DIG concentration and increasing DIG-POD concentration the S/N increases. At a concentration of the detection reagent of 300 mU/mL and of the capture reagent of 50 ng/mL a maximum of 36.3 can be seen.

In the following Table (determined for a detection reagent concentration of 300 mU/mL) it can be seen that the extinction increases up to a capture concentration of 50 ng/mL and decreases thereafter. Above this concentration avidity effects occur resulting in a decreased signal due to bivalent binding.

| STD [ng/ml] | c(Dig-POD) [mU/ml] | | | | | | | | | | |
|---|---|---|---|---|---|---|---|---|---|---|---|
| | 0 | | 0.5 | | 5.0 | | 50 | | 500 | | 5000 |
| | Ext. [OD] | CV [%] | Ext. [OD] | CV [%] | Ext. [OD] | CV [%] | Ext. [OD] | CV [%] | Ext. [OD] | CV [%] | Ext. [OD] | CV [%] |
| 50.0 | 0.047 | 20 | 0.113 | 0 | 0.679 | 3 | 2.087 | 0 | 0.412 | 10 | 0.061 | 2 |
| 25.0 | 0.036 | 6 | 0.089 | 4 | 0.440 | 3 | 1.073 | 2 | 0.208 | 4 | 0.045 | 2 |
| 12.5 | 0.036 | 4 | 0.076 | 7 | 0.287 | 0 | 0.544 | 0 | 0.120 | 2 | 0.040 | 4 |
| 6.25 | 0.035 | 4 | 0.055 | 3 | 0.176 | 1 | 0.283 | 1 | 0.075 | 2 | 0.037 | 2 |
| 3.13 | 0.035 | 6 | 0.046 | 3 | 0.109 | 0 | 0.161 | 3 | 0.056 | 0 | 0.034 | 0 |
| 1.56 | 0.036 | 2 | 0.043 | 5 | 0.072 | 0 | 0.097 | 1 | 0.046 | 2 | 0.034 | 4 |
| 0.78 | 0.030 | 14 | 0.037 | 4 | 0.054 | 1 | 0.066 | 1 | 0.038 | 2 | 0.029 | 2 |
| 0 | 0.035 | 10 | 0.037 | 2 | 0.038 | 0 | 0.039 | 2 | 0.036 | 2 | 0.033 | 0 |

It can be seen from the data in the following Table (detection after 18.5 min incubation time) that there is no difference in the dynamic range, i.e. no limitation due to the DIG-POD component. When assuming that above a signal twice the blank signal a good quantification is possible it can be seen that the sensitivity is independent of the DIG-POD concentration. Thus, the serial format using ABTS as color reagent has with a DIG-POD concentration of 300 mU/mL and 50 ng/mL capture reagent a detection range of from 1.56 ng/mL to 200 ng/mL.

| c(mAk <DIG> | DIG-POD [mU/mL] | | | | | |
|---|---|---|---|---|---|---|
| | 300 | | 600 | | 900 | |
| M-IgG) [ng/mL] | Ext. [OD] | CV [%] | Ext. [OD] | CV [%] | Ext. [OD] | CV [%] |
| 6400 | 2.897 | 3 | 2.950 | 1 | 2.874 | 0 |
| 3200 | 2.805 | 4 | 2.875 | 0 | 2.796 | 2 |
| 1600 | 2.806 | 2 | 2.852 | 1 | 2.831 | 2 |
| 800 | 2.673 | 1 | 2.741 | 0 | 2.766 | 2 |
| 400 | 2.486 | 0 | 2.537 | 2 | 2.603 | 0 |
| 200 | 2.277 | 2 | 2.342 | 0 | 2.436 | 1 |
| 100 | 1.721 | 0 | 1.769 | 0 | 1.958 | 0 |
| 50.0 | 1.107 | 0 | 1.127 | 1 | 1.328 | 2 |
| 25.0 | 0.595 | 1 | 0.621 | 1 | 0.751 | 1 |
| 12.5 | 0.304 | 1 | 0.316 | 0 | 0.394 | 4 |
| 6.25 | 0.168 | 0 | 0.172 | 1 | 0.214 | 0 |
| 3.13 | 0.099 | 1 | 0.105 | 1 | 0.128 | 1 |
| 1.56 | 0.063 | 2 | 0.069 | 2 | 0.079 | 2 |
| 0.78 | 0.046 | 0 | 0.051 | 1 | 0.055 | 1 |
| 0.39 | 0.036 | 4 | 0.040 | 4 | 0.055 | 31 |
| 0 | 0.028 | 8 | 0.032 | 9 | 0.036 | 10 |

The reaction has been repeated using TMB as color substrate. It has been found that when using TMB instead of ABTS the assay can be performed in a shorter time, i.e. it is quicker, and higher extinction values can be obtained. The detection range using TMB is 0.78 ng/mL to 50 ng/mL. The values are shown in the following Table.

| c(mAk <DIG> | DIG-POD [mU/mL] | | | | | |
|---|---|---|---|---|---|---|
| | 300 | | 100 | | 50 | |
| M-IgG) [ng/mL] | Ext. [OD] | CV [%] | Ext. [OD] | CV [%] | Ext. [OD] | CV [%] |
| 6400 | 3.499 | 6 | 3.686 | 0 | 3.569 | 5 |
| 3200 | 3.465 | 9 | 3.138 | 0 | 3.426 | 0 |
| 1600 | 3.508 | 11 | 3.734 | 0 | 3.551 | 4 |
| 800 | 3.506 | 5 | 3.301 | 0 | 3.521 | 0 |
| 400 | 3.603 | 13 | 3.435 | 0 | 3.349 | 4 |
| 200 | 3.490 | 5 | 3.464 | 5 | 3.358 | 2 |
| 100 | 3.296 | 5 | 3.258 | 0 | 3.103 | 3 |
| 50.0 | 2.596 | 1 | 2.239 | 1 | 2.046 | 1 |
| 25.0 | 1.405 | 1 | 1.176 | 0 | 1.076 | 2 |
| 12.5 | 0.693 | 1 | 0.573 | 0 | 0.530 | 4 |
| 6.25 | 0.348 | 1 | 0.292 | 0 | 0.268 | 3 |
| 3.13 | 0.184 | 1 | 0.157 | 0 | 0.149 | 1 |
| 1.56 | 0.107 | 0 | 0.095 | 1 | 0.085 | 2 |
| 0.78 | 0.068 | 3 | 0.062 | 0 | 0.056 | 1 |
| 0.39 | 0.050 | 6 | 0.046 | 0 | 0.044 | 6 |
| 0 | 0.033 | 2 | 0.032 | 0 | 0.030 | 0 |

2) Pre-Incubation Analyte and Detection Reagent

From the following Table can be seen that at a concentration of 50 ng/mL of the monoclonal anti-digoxygenin antibody the S/N increases with increasing coating concentration and concomitant reduced detection reagent. At 400 ng/mL BI-RPLA-DIG and 31.3 mU/mL DIG-POD a maximum is reached. The color reagent was ABTS.

| c(BI-RPLA-DIG) [ng/mL] | c(DIG-POD) [mU/mL] | | | | | |
|---|---|---|---|---|---|---|
| | 1000 | 500 | 250 | 125 | 62.5 | 31.3 |
| | S/N | | | | | |
| 400 | 3.4 | 5.4 | 11.1 | 19.6 | 38.0 | 53.3 |
| 200 | 2.5 | 5.0 | 9.3 | 18.5 | 34.9 | 51.0 |
| 100 | 2.0 | 3.1 | 5.6 | 10.7 | 23.8 | 42.2 |
| 75 | 1.3 | 2.9 | 5.1 | 10.2 | 21.3 | 38.9 |
| 50 | 1.6 | 2.2 | 4.4 | 7.2 | 16.9 | 33.1 |
| 25 | 1.3 | 1.8 | 2.6 | 4.2 | 9.4 | 20.0 |
| 10 | 1.1 | 1.2 | 1.7 | 2.5 | 4.5 | 10.1 |
| 5 | 1.1 | 0.9 | 1.3 | 1.7 | 2.8 | 6.3 |

In all three DIG-POD concentrations tested in the following series a hook-effect starting at the anti-digoxygenin antibody concentration of 400 ng/mL can be seen. It can further be seen that with increasing DIG-POD concentration the saturation plateau is getting broader and the hook effect is reached later. A clear limitation by the POD concentration can be seen. For this assay at a BI-RPLA-DIG concentration of 400 ng/mL and a DIG-POD concentration of 30 mU/mL the assay has a detection range of from 3.13 ng/mL to 150 ng/mL. The other two concentrations are not suitable due to the limited POD effect and the longer required time.

| c(mAk |   | DIG-POD [mU/mL] |   |   |   |
|---|---|---|---|---|---|
| <DIG>) | 30 | | 15 | | 7.5 |
| M-IgG) [ng/mL] | Ext. [OD] | CV [%] | Ext. [OD] | CV [%] | Ext. [OD] | CV [%] |
| 6400 | 1.352 | 2 | 0.739 | 1 | 0.401 | 1 |
| 3200 | 1.880 | 2 | 1.134 | 0 | 0.640 | 0 |
| 1600 | 2.405 | 1 | 1.676 | 1 | 1.048 | 0 |
| 800 | 2.751 | 0 | 2.212 | 2 | 1.553 | 0 |
| 400 | 2.704 | 0 | 2.249 | 1 | 1.683 | 2 |
| 200 | 2.563 | 1 | 2.047 | 1 | 1.486 | 2 |
| 100 | 1.898 | 1 | 1.668 | 2 | 1.232 | 3 |
| 50.0 | 0.919 | 1 | 1.170 | 0 | 0.969 | 2 |
| 25.0 | 0.392 | 1 | 0.647 | 12 | 0.692 | 3 |
| 12.5 | 0.160 | 2 | 0.227 | 1 | 0.287 | 3 |
| 6.25 | 0.077 | 2 | 0.098 | 1 | 0.102 | 3 |
| 3.13 | 0.044 | 2 | 0.050 | 1 | 0.053 | 3 |
| 1.56 | 0.031 | 2 | 0.032 | 0 | 0.033 | 4 |
| 0.78 | 0.026 | 0 | 0.027 | 3 | 0.025 | 6 |
| 0.39 | 0.023 | 0 | 0.023 | 0 | 0.023 | 3 |
| 0 | 0.022 | 0 | 0.023 | 3 | 0.022 | 6 |

3) Pre-Incubation of Capture Reagent, Analyte and Detection Reagent

From the data in the following Table it can be seen that at a concentration of 50 ng/mL of the monoclonal anti-digoxygenin antibody the S/N increases with decreasing capture reagent concentration as well as decreasing detection reagent concentration. At a concentration of 13.7 ng/mL of BI-RPLA-DIG and 18.8 mU/mL of DIG-POD a maximum is reached. The color reagent was ABTS.

| c(BI-RPLA-DIG) [ng/mL] | c(DIG-POD) [mU/mL] | | | | | |
|---|---|---|---|---|---|---|
| | 600 | 300 | 150 | 75 | 37.5 | 18.8 |
| | | | S/N | | | |
| 10000 | 6.1 | 3.6 | 2.5 | 1.8 | 1.5 | 1.1 |
| 3333 | 22.0 | 14.0 | 9.5 | 5.5 | 3.9 | 2.5 |
| 1111 | 30.9 | 26.4 | 25.6 | 16.4 | 11.4 | 6.3 |
| 370 | 34.0 | 39.9 | 36.1 | 28.8 | 21.5 | 13.0 |
| 123 | 20.7 | 28.3 | 36.9 | 39.4 | 35.6 | 25.3 |
| 41.2 | 9.3 | 15.0 | 25.2 | 36.1 | 47.3 | 47.5 |
| 13.7 | 4.1 | 6.6 | 10.1 | 22.1 | 37.2 | 48.8 |
| 4.57 | 1.1 | 1.2 | 1.0 | 1.0 | 1.0 | 0.8 |

From the following data set it can be seen that at a BI-RPLA-DIG concentration of 10 ng/mL to a DIG-POD concentration of 16.6 mU/mL a limitation occurs and the standard curve does not reach an OD value of 2. For this combination also a hook effect is visible at an analyte concentration of 200 ng/mL. As the data is comparable the criterion is the reagent use for selecting one of these in this category. No hook effect is detectable up to an analyte concentration of 6400 ng/mL. The detection range at a BI-RPLA-DIG concentration of 1000 ng/mL and a DIG-POD concentration of 600 mU/mL is 3.13 ng/mL to 200 ng/mL. The same detection range has an assay using 100 ng/mL BI-RPLA-DIG and 100 mU/mL DIG-POD.

| | DIG-POD [mU/mL] | | | | | |
|---|---|---|---|---|---|---|
| | 600 | | 100 | | 16.6 | |
| c(mAk <DIG>) | BI-RPLA-DIG [ng/mL] | | | | | |
| | 1000 | | 100 | | 10 | |
| M-IgG) [ng/mL] | Ext. [OD] | CV [%] | Ext. [OD] | CV [%] | Ext. [OD] | CV [%] |
| 6400 | 3.005 | 0 | 2.933 | 0 | 0.294 | 0 |
| 3200 | 2.973 | 0 | 2.940 | 1 | 0.415 | 0 |
| 1600 | 3.054 | 1 | 3.023 | 1 | 0.573 | 1 |
| 800 | 2.931 | 1 | 2.975 | 1 | 0.739 | 1 |
| 400 | 2.788 | 1 | 2.915 | 0 | 0.874 | 1 |
| 200 | 2.243 | 2 | 2.420 | 1 | 1.018 | 1 |
| 100 | 1.350 | 3 | 1.339 | 2 | 1.065 | 1 |
| 50.0 | 0.804 | 0 | 0.650 | 3 | 0.781 | 2 |
| 25.0 | 0.404 | 2 | 0.346 | 2 | 0.331 | 1 |
| 12.5 | 0.207 | 1 | 0.154 | 2 | 0.130 | 1 |
| 6.25 | 0.118 | 3 | 0.086 | 2 | 0.064 | 3 |
| 3.13 | 0.073 | 4 | 0.053 | 3 | 0.040 | 4 |
| 1.56 | 0.049 | 9 | 0.037 | 4 | 0.029 | 10 |
| 0.78 | 0.038 | 4 | 0.030 | 0 | 0.025 | 9 |
| 0.39 | 0.031 | 0 | 0.025 | 0 | 0.021 | 17 |
| 0 | 0.026 | 3 | 0.024 | 0 | 0.023 | 9 |

Example 4

Different Color Reagents

The extinction value shaded in the next Table for the different color reagents ABTS and TMB and the emission values for HPPA, respectively, are below the detection limit and cannot be quantified. It can be seen that the assay in the serial setup (the assay as reported herein) has a detection limit using TMB of 0.94 ng/mL in is thereby two times more sensitive compared to ABTS. Using HPPA the detection limit is 0.47 ng/mL (using the standard series with 5 U/mL DIG-POD). Although this assay variant is more sensitive than the assay using TMB surprisingly the assay signal could not be obtained in a sufficiently reproducible manner to allow the setup of a robust assay.

| ABTS: | | | | | | | | | | | | |
|---|---|---|---|---|---|---|---|---|---|---|---|---|
| | c(Dig-POD) [mU/ml] | | | | | | | | | | | |
| | 15 | | 10 | | 5 | | 1 | | 0.5 | | 0.1 | |
| STD [ng/ml] | Ext [OD] | S:N | Ext [OD] | S:N | Ext [OD] | S:N | Ext [OD] | S:N | Ext [OD] | S:N | Ext. [OD] | S:N |
| 60.0 | 2.207 | 13.3 | 2.074 | 16.8 | 1.905 | 20.9 | 1.530 | 47.1 | 1.370 | 39.1 | 1.025 | 40.2 |
| 30.0 | 1.362 | 8.2 | 1.220 | 9.9 | 1.066 | 11.7 | 0.794 | 24.4 | 0.682 | 19.5 | 0.485 | 19.0 |
| 15.0 | 0.858 | 5.2 | 0.723 | 5.9 | 0.585 | 6.4 | 0.405 | 12.5 | 0.346 | 9.9 | 0.238 | 9.3 |
| 7.50 | 0.503 | 3.0 | 0.380 | 3.1 | 0.318 | 3.5 | 0.213 | 6.5 | 0.184 | 5.3 | 0.131 | 5.1 |
| 3.75 | 0.352 | 2.1 | 0.260 | 2.1 | 0.204 | 2.2 | 0.122 | 3.8 | 0.104 | 3.0 | 0.076 | 3.0 |
| 1.88 | 0.281 | 1.7 | 0.190 | 1.5 | 0.138 | 1.5 | 0.078 | 2.4 | 0.066 | 1.9 | 0.049 | 1.9 |
| 0.94 | 0.200 | 1.2 | 0.176 | 1.4 | 0.111 | 1.2 | 0.055 | 1.7 | 0.052 | 1.5 | 0.037 | 1.5 |
| 0 | 0.166 | 1.0 | 0.124 | 1.0 | 0.091 | 1.0 | 0.033 | 1.0 | 0.035 | 1.0 | 0.026 | 1.0 |

| | TMB: | | | | | | | | | | |
|---|---|---|---|---|---|---|---|---|---|---|---|
| | c(Dig-POD)[mU/ml] | | | | | | | | | | |
| | 15 | | 10 | | 5 | | 1 | | 0.5 | | 0.1 |
| STD [ng/ml] | Ext [OD] | S:N | Ext [OD] | S:N | Ext [OD] | S:N | Ext [OD] | S:N | Ext [OD] | S:N | Ext. [OD] | S:N |

| STD [ng/ml] | Ext [OD] | S:N | Ext [OD] | S:N | Ext [OD] | S:N | Ext [OD] | S:N | Ext [OD] | S:N | Ext. [OD] | S:N |
|---|---|---|---|---|---|---|---|---|---|---|---|---|
| 60.0 | 3.585 | 4.0 | 3.506 | 6.7 | 3.516 | 13.5 | 3.476 | 44.6 | 3.395 | 58.5 | 3.146 | 71.5 |
| 30.0 | 3.447 | 3.9 | 3.364 | 6.4 | 3.229 | 12.4 | 2.888 | 37.0 | 2.608 | 45.0 | 1.951 | 44.3 |
| 15.0 | 2.990 | 3.4 | 2.755 | 5.2 | 2.354 | 9.0 | 1.669 | 21.4 | 1.421 | 24.5 | 0.982 | 22.3 |
| 7.50 | 2.282 | 2.6 | 1.870 | 3.6 | 1.359 | 5.2 | 0.881 | 11.3 | 0.748 | 12.9 | 0.510 | 11.6 |
| 3.75 | 1.656 | 1.9 | 1.223 | 2.3 | 0.905 | 3.5 | 0.489 | 6.3 | 0.398 | 6.9 | 0.271 | 6.2 |
| 1.88 | 1.190 | 1.3 | 0.957 | 1.8 | 0.631 | 2.4 | 0.293 | 3.8 | 0.236 | 4.1 | 0.156 | 3.5 |
| 0.94 | 0.808 | 0.9 | 0.803 | 1.5 | 0.390 | 1.5 | 0.202 | 2.6 | 0.147 | 2.5 | 0.099 | 2.3 |
| 0 | 0.856 | 1.0 | 0.526 | 1.0 | 0.261 | 1.0 | 0.078 | 1.0 | 0.058 | 1.0 | 0.044 | 1.0 |

| | HPPA: | | | | | | | | | | |
|---|---|---|---|---|---|---|---|---|---|---|---|
| | c(Dig-POD) [mU/ml] | | | | | | | | | | |
| STD | 10 | | 5 | | 1 | | 0.5 | | 0.1 | | 0.05 |
| [ng/ml] | [FU] | S:N | [FU] | S:N | [FU] | S:N | [FU] | S:N | [FU] | S:N | [FU] | S:N |
| 15.0 | 44824 | 26.7 | 38558 | 52.6 | 27790 | 83.0 | 23087 | 95.0 | 14700 | 61.2 | 11761 | 50.5 |
| 7.50 | 24711 | 14.7 | 19836 | 27.0 | 13058 | 39.0 | 10388 | 42.7 | 6497 | 27.1 | 4927 | 21.1 |
| 3.75 | 13976 | 8.3 | 10101 | 13.8 | 6227 | 18.6 | 4843 | 19.9 | 2839 | 11.8 | 2144 | 9.2 |
| 1.88 | 7604 | 4.5 | 5106 | 7.0 | 2765 | 8.3 | 2145 | 8.8 | 1158 | 4.8 | 882 | 3.8 |
| 0.94 | 4726 | 2.8 | 3077 | 4.2 | 1267 | 3.8 | 950 | 3.9 | 516 | 2.1 | 428 | 1.8 |
| 0.47 | 2558 | 1.5 | 1558 | 2.1 | 571 | 1.7 | 426 | 1.8 | 293 | 1.2 | 266 | 1.1 |
| 0.23 | 1677 | 1.0 | 1009 | 1.4 | 381 | 1.1 | 315 | 1.3 | 257 | 1.1 | 238 | 1.0 |
| 0 | 1681 | 1.0 | 734 | 1.0 | 335 | 1.0 | 243 | 1.0 | 240 | 1.0 | 233 | 1.0 |

Example 5

Matrix Range

It can be seen from the following Table that in different matrices the spiked standard samples compared to the standard samples produced with buffer only the obtained signal is reduced. Referencing to the buffer samples the spiked standards are recovered with 94% to 72% from the different sample matrices. The variation is 3% to 5%. Thus, there is no significant difference between all the matrices.

| c(mAk<DIG>M-IgG) [ng/mL] | matrix average | | | |
|---|---|---|---|---|
| | Ext. [OD] | recov. [%] | SD [OD] | CV [%] |
| STA D: 35.0 | 1.349 | 83 | 0.065 | 5 |
| STD B: 17.5 | 0.680 | 84 | 0.020 | 3 |
| STD C: 8.75 | 0.357 | 84 | 0.011 | 3 |
| STD D: 4.38 | 0.199 | 84 | 0.008 | 4 |

| c(mAk<DIG> M-IgG) [ng/mL] | buffer | | human | | minipig | | cynomolgus | | mouse | | beagle | |
|---|---|---|---|---|---|---|---|---|---|---|---|---|
| | Ext. [OD] | recov. [%] | Ext. [OD] | recov. [%] | Ext. [OD] | recov. [%] | Ext. [OD] | recov. [%] | Ext. [OD] | recov. [%] | Ext. [OD] | recov. [%] |
| STA D: 35.0 | 1.627 | 100 | 1.392 | 86 | 1.374 | 85 | 1.255 | 77 | 1.414 | 87 | 1.311 | 81 |
| STD B: 17.5 | 0.810 | 100 | 0.681 | 84 | 0.691 | 85 | 0.662 | 81 | 0.708 | 87 | 0.661 | 81 |
| STD C: 8.75 | 0.419 | 100 | 0.361 | 85 | 0.365 | 86 | 0.347 | 81 | 0.368 | 87 | 0.342 | 80 |
| STD D: 4.38 | 0.229 | 100 | 0.199 | 84 | 0.208 | 89 | 0.194 | 82 | 0.206 | 88 | 0.190 | 79 |
| STD E: 2.39 | 0.134 | 98 | 0.115 | 77 | 0.125 | 89 | 0.117 | 80 | 0.123 | 86 | 0.112 | 74 |
| STD F: 1.09 | 0.090 | 101 | 0.078 | 74 | 0.086 | 93 | 0.080 | 79 | 0.083 | 86 | 0.077 | 72 |
| STD G: 0.55 | 0.067 | 101 | 0.056 | 55 | 0.066 | 94 | 0.061 | 77 | 0.061 | 77 | 0.061 | 77 |
| blank | 0.044 | — | 0.041 | — | 0.047 | — | 0.044 | — | 0.046 | — | 0.045 | — |

-continued

| c(mAk<DIG>M-IgG) [ng/mL] | Ext. [OD] | matrix average recov. [%] | SD [OD] | CV [%] |
|---|---|---|---|---|
| STD E: 2.39 | 0.118 | 81 | 0.006 | 5 |
| STD F: 1.09 | 0.081 | 81 | 0.004 | 5 |
| STD G: 0.55 | 0.061 | 76 | 0.003 | 5 |
| blank | 0.044 | — | 0.002 | 5 |

Example 6

Assay Characteristics

Figure 3:
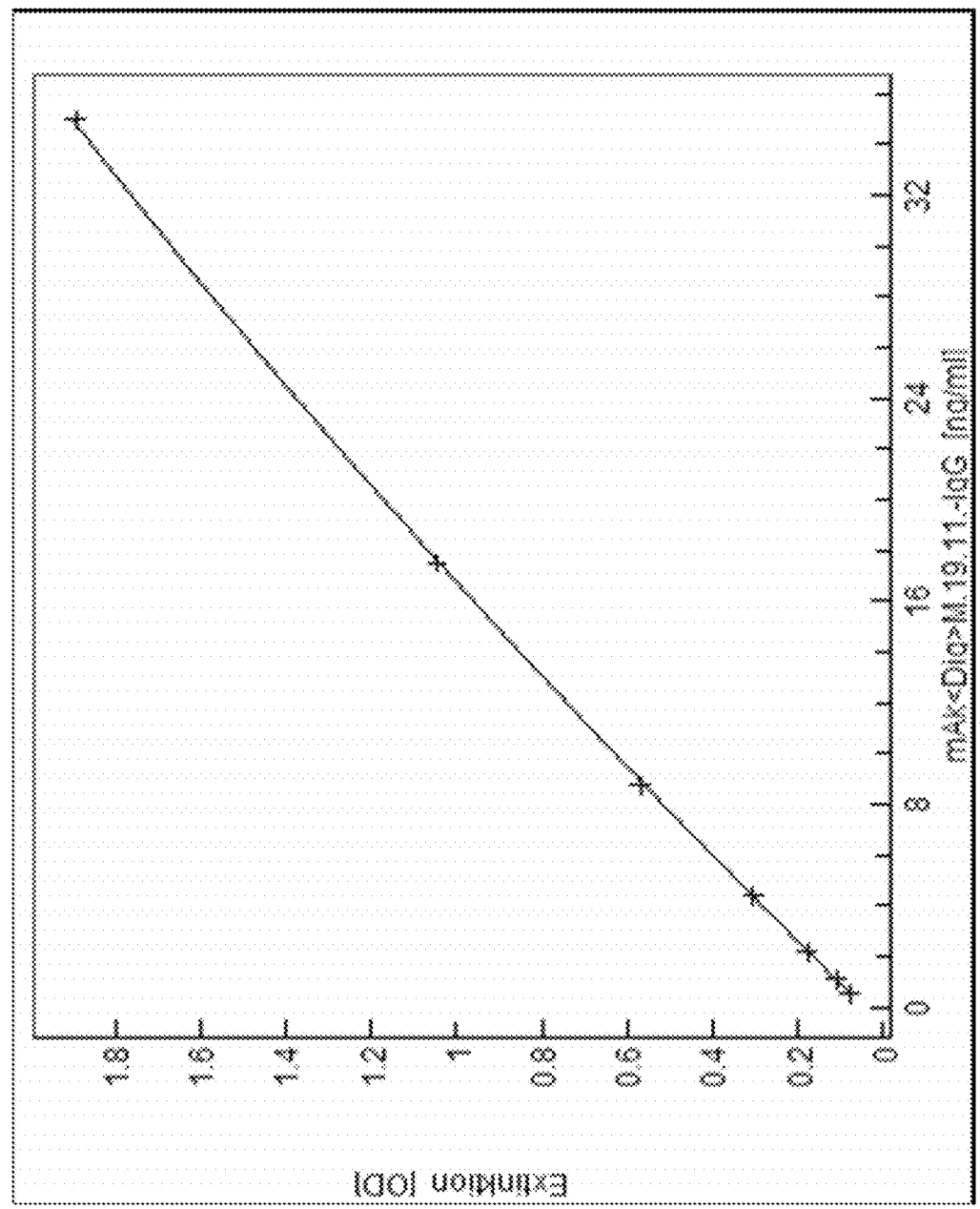
FIG. 3 Assay standard curve.

In FIG. 3 standard curve for the assay as reported herein is presented comprising STD A to STD G and a blank value. The detection range is from 0.55 ng/mL to 35 ng/mL based on the weight of the employed anti-digoxygenin antibody. The following Table provides the respective data.

| assay conc. [ng/mL] | 35 | 17.5 | 8.75 | 4.38 | 2.19 | 1.09 | 0.55 | 0 |
|---|---|---|---|---|---|---|---|---|
| plasma conc. [ng/mL] | 350 | 175 | 87.5 | 43.8 | 21.9 | 10.9 | 5.5 | 0 |
| average signal [OD] | 1.903 | 1.036 | 0.539 | 0.288 | 0.164 | 0.103 | 0.071 | 0.042 |
| SD signal [OD] | 0.030 | 0.044 | 0.027 | 0.015 | 0.007 | 0.006 | 0.003 | 0.004 |

The assay as reported herein has an intra-assay precision with a standard deviation/coefficient of variation of 2% to 6%. The intra-assay recovery rate is between 100% and 104%.

The assay as reported herein has an inter-assay precision with a standard deviation/coefficient of variation of 5% to 12%. The inter-assay recovery rate is between 78 and 117%. The calculated recover rate for the μL- and LLQC samples is between 87% and 121% and, thus, within the acceptable range of 25%.

Example 7

Selectivity

From the following Table can be seen that the assay has a very good selectivity. The extinction values determined for the different antibodies are well below the lowest standard sample approximately at blank sample level. Thus, capture and tracer reagent are not linked to each other up to a concentration of 10 μg/mL. Thus, the assay is specific for the anti-digoxygenin antibody.

The assay as reported herein shows no hook effect up to a concentration of 100 μg/mL antibody in 100% pooled plasma (assay concentration 10 μg/mL). The following Table provides the respective determined values. Samples (if applicable after dilution) are detected within the acceptance interval of 80% to 120% recovery (AQL=above limit of quantification; BQL=below limit of quantification).

| dilution factor to highest concentrated sample | plasma conc. [ng/mL] | signal [OD] | calc. conc. [ng/ml] | recovery [%] |
|---|---|---|---|---|
| — | 100000 | 3.504 | ALQ | — |
| 10 | 10000 | 3.658 | ALQ | — |
| 100 | 1000 | 3.464 | ALQ | — |
| 300 | 333.3 | 2.032 | 384.3 | 115.3 |
| 900 | 111.1 | 0.728 | 126.8 | 114.1 |
| 2700 | 37.04 | 0.274 | 43.30 | 116.9 |
| 8100 | 12.35 | 0.113 | 14.26 | 115.5 |
| 24300 | 4.115 | 0.061 | BLQ | — |

-continued

| dilution factor to highest concentrated sample | plasma conc. [ng/mL] | signal [OD] | calc. conc. [ng/ml] | recovery [%] |
|---|---|---|---|---|
| recovery range [%] | — | — | 114.1-116.9 | |

The dilution linearity of the assay as reported herein has been tested in plasma concentrations of up to 100 μg/mL anti-digoxygenin antibody in eight minipig individual plasmas. 41 out of the 45 diluted samples have been detected within the acceptance interval of 80% to 120% (all 45 dilutions in the interval of 81% to 138%). The different plasma matrices have no significant influence on the recovery of the analyte.

Example 8

Sample Quantification

From the following Tables it can be seen that by exchanging individual amino acid residues in the Fc-region of

Figure 4:
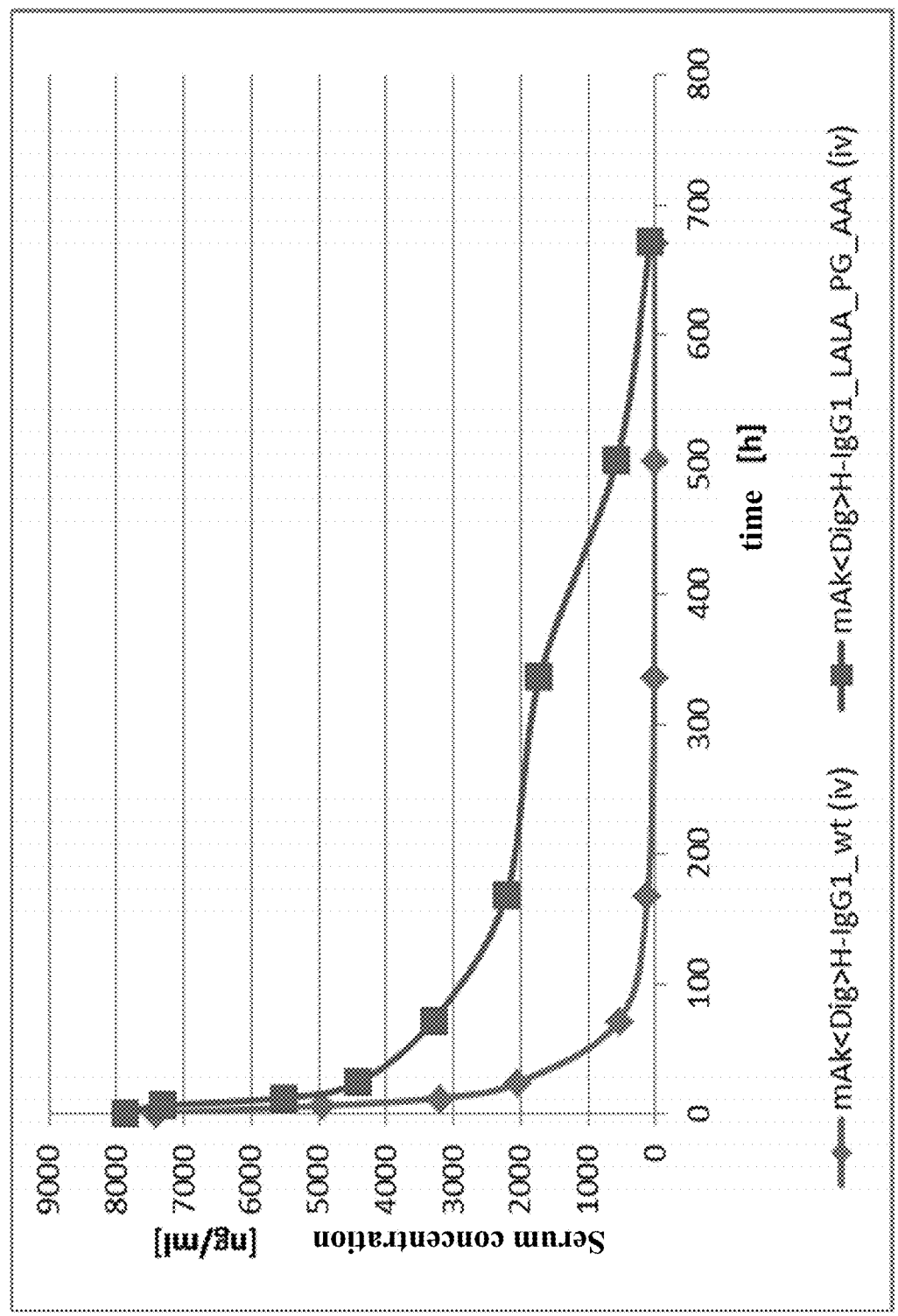
FIG. 4 Pharmacokinetic analysis of a wild-type antibody (diamond) and LALA-PG-AAA mutant (square).

| STD-conc. [ng/mL] | extinction [OD] | | | | | analyte conc. [ng/mL] |
|---|---|---|---|---|---|---|
| | STD A-H | A1 | A3 | A5 | A7 | |
| 35.0 | 1.873 | 0.048 | 0.052 | 0.046 | 0.045 | 10000 |
| 17.5 | 1.044 | 0.045 | 0.044 | 0.038 | 0.050 | 1000 |
| 8.75 | 0.541 | 0.054 | 0.046 | 0.041 | 0.040 | 100 |
| 4.38 | 0.293 | 0.042 | 0.042 | 0.040 | 0.041 | 10 |
| 2.19 | 0.160 | 0.044 | 0.051 | 0.041 | 0.041 | 10000 |
| 1.09 | 0.097 | 0.044 | 0.043 | 0.042 | 0.042 | 1000 |
| 0.55 | 0.071 | 0.044 | 0.043 | 0.042 | 0.049 | 100 |
| 0 | 0.044 | 0.052 | 0.046 | 0.043 | 0.048 | 10 |
| | | A2 | A4 | A6 | A8 | | antibodies the pharmacokinetic half-life has been changed (see FIG. 4). The data has been generated by determining in 16 different minipig sera. Shaded values are below the limit of quantification, ivt denotes intravitreal application and iv denotes intravenous application.

| sampling time point [h] | c(mAk<Dig>H-IgG1_wt) [ng/mL] | | | | | | | |
|---|---|---|---|---|---|---|---|---|
| | group 4 (ivt) | | | | | | group 7 (iv) | |
| | 19 | 20 | 21 | 22 | 23 | 24 | 29 | 30 |
| 0.5 | — | — | — | — | — | — | 7931 | 7808 |
| 6 | — | — | — | — | — | — | 7246 | 7383 |
| 12 | 132 | 174 | 559 | 109 | 112 | 14.7 | 5351 | 5673 |
| 24 | 235 | 416 | 758 | 194 | 341 | 57.6 | 4197 | 4641 |
| 48 | 377 | 621 | 953 | 382 | 602 | 151 | — | — |
| 72 | 463 | 667 | 923 | 427 | 560 | 258 | 3031 | 3564 |
| 168 | 710 | 892 | 958 | 606 | 828 | 768 | 2220 | — |
| 336 | — | — | 932 | 25.8 | 273 | 1089 | 1722 | — |
| 504 | — | — | — | — | −4.6 | 1431 | 574 | — |
| 672 | — | — | — | — | −1.9 | 1225 | 70.9 | — |

| sampling time point [h] | c(mAk<Dig>H-IgG1_LALA_PG_AAA) [ng/mL] | | | | | | | |
|---|---|---|---|---|---|---|---|---|
| | group 3 (ivt) | | | | | | group 6 (iv) | |
| | 13 | 14 | 151 | 61 | 17 | 18 | 27 | 28 |
| 0.5 | — | — | — | — | — | — | 7,691 | 7,142 |
| 6 | — | — | — | — | — | — | 4,984 | 4,891 |
| 12 | 269 | 21.2 | 99.1 | 300 | 58.5 | 91.3 | 3,279 | 3,104 |
| 24 | 304 | 102 | 179 | 612 | 95.5 | 162 | 2082 | 1989 |
| 48 | 319 | 141 | 268 | 654 | 196 | 239 | — | — |
| 72 | 259 | 143 | 208 | 567 | 230 | 232 | 560 | 514 |
| 168 | 79.0 | 373 | 155 | 349 | 316 | 288 | 111 | 125 |
| 336 | — | — | 110 | 243 | 170 | 161 | 15.4 | 0.0 |
| 504 | — | — | — | — | 103 | 31.0 | 6.3 | 0.0 |
| 672 | — | — | — | — | 70.4 | 16.9 | 4.5 | 0.0 |

Figure 5:
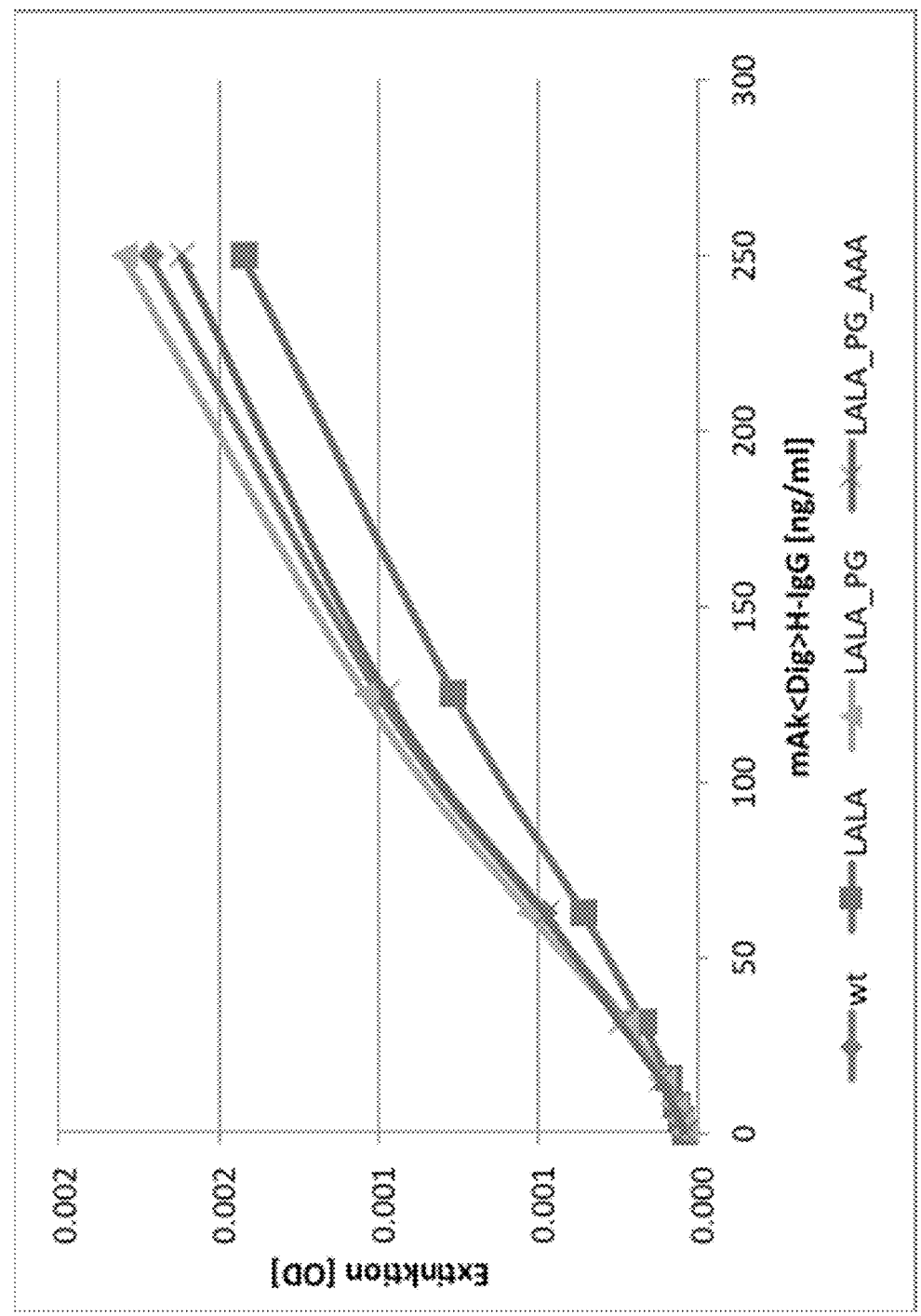
FIG. 5 Standard curves.

The three Fc-region modified antibodies have been detected using the assay as reported herein. The standard curve is shown in FIG. 5 and the respective date in the Table below.

| wild-type ng/mL | LALA-mutant | | LALAPG-mutant | | LALAPGAAA-mutant | |
|---|---|---|---|---|---|---|
| | calc. conc. ng/ml | recovery % | calc. conc. ng/ml | recovery % | calc. conc. ng/ml | Recovery % |
| 250 | 193 | 77 | 251 | 100 | 230 | 92 |
| 125 | 95.6 | 76 | 131 | 105 | 122 | 98 |
| 62.5 | 47.8 | 77 | 67.1 | 107 | 61.5 | 98 |
| 31.3 | 25.2 | 81 | 32.2 | 103 | 33.6 | 107 |
| 15.6 | 12.5 | 80 | 16.6 | 106 | 16.7 | 107 |
| 7.81 | 6.67 | 85 | 8.38 | 107 | 8.38 | 107 |
| 3.91 | 4.02 | 103 | 4.14 | 106 | 4.14 | 106 |

LITERATURE

Carl Roth GmbH und Co. KG: *Albumine für die Biochemie und Molekularbiologie*. ILK January 2009

Diamandis E. P., Christopoulos T. K. (1991) The biotin-(strept)avidin system: principles and applications in biotechnology. *Clinical Chemistry*, 37, 625-636

European Medicines Agency (July 2011), Guideline on bioanalytical method validation Goebel-Stengel M, Stengel A, Taché Y, Reeve J R (2011) The importance of using the optimal plastic ware and glassware in studies involving peptides. *Analytical Biochemistry*, 414, 38-46

Hoffmann-La Roche AG: *Roche Lexikon—Medizin*. 5. Ed. Munich: Urban & Fischer, 2003

Holländer, Georg: *Immunologie—Grundlage für Klinik und Praxis*. 1. Ed. Munich: Urban & Fischer, 2006

Issaq H J, Xiao Z, Veenstra T D (2007) Serum and Plasma Proteomics. *Chemical Reviews*, 107(8), 3601-3620

Luttmann et al.: *Der Experimentator—Immunologie*. 3. Ed. Heidelberg: Spektrum Akademischer Verlag, 2009

Mould D. R., Green B. (2010) Pharmacokinetics and pharmacodynamics of monoclonal antibodies: concepts and lessons for drug development. *BioDrugs*, 24(1), 23-39

Raem, A.; Rauch, P.: *Immunoassays*. 1. Ed. Munich: Spektrum Akademischer Verlag, 2007

Simpson J. R., Greening D. W: *Serum/Plasma Proteomics*. 1 vol. Totowa: Humana Press Inc., 2011

Stubhan, Miriam: Das Göttinger Minipig als Telemetriemodell für pharmakologische Zwecke, Diss. Univ. Munich, 2008

U.S. Department of Health and Human Services, Food and Drug Administration, Center for Drug Evaluation and Research, Center for Veterinary Medicine (May 2001), *Guidance for Industry—Bioanalytical Method Validation*

ABBREVIATIONS

ABTS 2,2'-Azino-di-(3-ethylbenzthiazoline-6-sµLfonic acid)
Ak antibody
ALQ Above limit of quantification
AP Assay buffer (=Universal-buffer)
AS amino acid
Bi Biotin
BLQ Below limit of quantification
BSA Bovine serum albumin
CDR Complementarity determining region
CV Coefficient of variation
Dig Digoxigenin
ELISA Enzyme Linked Immunosorbent Assay
F(ab')$_2$ Fragment antigen binding (bivalent)
Fab Fragment antigen binding (monovalent)
FC Fragment Crystallizable
H Human
HPPA 3-(4-Hydroxyphenyl)-propionic acid
HRP Horseradish peroxidase
Ig Immunoglobulin
IgA Immunoglobulin of subclass A
IgD Immunoglobulin of subclass D
IgE Immunoglobulin of subclass E
IgG Immunoglobulin of subclass G
IgM Immunoglobulin of subclass M
M mouse
mAk monoclonal antibody
MTP micro titer plate
OD optical density
pAk polyclonal antibody
POD Peroxidase
PP Polypropylene
PS Polystyrol
Rb Rabbit
RFU Relative fluorescence units
RPLA bovine plasma albumin
SA Streptavidin
S:N Signal-to-noise ratio
SD Standard deviation
STD Standard
TMB 3,3',5,5'-Tetramethylbenzidine
XOSu X(ε-Aminocaproic acid)-O-Succinimide

The invention claimed is:

1. A method for the determination of the amount of an anti-hapten non-therapeutic Fc-modified bivalent antibody in a serum or plasma sample obtained from a non-human experimental animal, whereby the antibody comprises one or more mutations in the Fc-region compared to the corresponding wild-type Fc-region that has a sequence of SEQ ID NO: 01, 02, or 03, wherein detection of the antibody is independent from of Fc region modification, wherein the method comprises the following steps in the following order:
   (a) providing a biotinylated bovine plasma albumin (RPLA) to which more than one copy of the hapten antigen is chemically conjugated thereon to form a biotinylated bovine plasma albumin (RPLA)-hapten capture reagent,
   (b) immobilizing the capture reagent of (a) on a streptavidin or avidin conjugated on a solid surface, wherein the biotinylated bovine plasma albumin (RPLA)-hapten capture reagent has a coating density of about 50 ng/ml,
   (c) incubating the capture reagent of (b), with the sample comprising the anti-hapten non-therapeutic Fc-modified bivalent antibody to form an immobilized antigen-antibody complex, wherein the anti-hapten antibody is selected from the group consisting of an anti-biotin antibody, an anti-digoxygenin antibody, an anti-theophylline antibody, an anti-helicar antibody, and an anti-bromodeoxyuridine antibody,
   (d) incubating the immobilized antigen-antibody complex of (c) with the hapten antigen of said antibody, wherein the hapten is conjugated to a detectable label to form an immobilized ternary complex,
   (e) determining the amount of the antibody by determining the amount of the detectable label in the immobilized ternary complex; and
   (f) evaluating the antibody in the experimental animal for pharmacokinetic properties associated with Fc-region mutations, wherein the antibody is quantified at serial time points by performing steps (a)-(e),
   wherein the hapten antigen is not present in the experimental animal from which the analyzed sample is obtained.

2. The method according to claim 1, wherein the detectable label is an enzyme.

3. The method according to claim 1, wherein the detectable label is a peroxidase.

4. The method according to claim 3, wherein the detectable label is horseradish peroxidase.

5. The method according to claim 2, wherein the concentration of the detectable label is about 300 mU/mL.

6. The method according to claim 3, wherein the determining is by incubating the immobilized ternary complex with 3,3',5,5'-tetramethyl benzidine.

* * * * *